United States Patent
Kawamura

(10) Patent No.: US 12,127,850 B2
(45) Date of Patent: Oct. 29, 2024

(54) MOTOR ORGAN DISEASE PREDICTION DEVICE, MOTOR ORGAN DISEASE PREDICTION METHOD, MOTOR ORGAN DISEASE PREDICTION PROGRAM, LEARNING DEVICE, LEARNING METHOD, LEARNING PROGRAM, AND LEARNED NEURAL NETWORK

(71) Applicant: FUJIFILM CORPORATION, Tokyo (JP)

(72) Inventor: Takahiro Kawamura, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 369 days.

(21) Appl. No.: 17/577,345

(22) Filed: Jan. 17, 2022

(65) Prior Publication Data
US 2022/0249013 A1    Aug. 11, 2022

(30) Foreign Application Priority Data

Feb. 9, 2021   (JP) .................. 2021-019232

(51) Int. Cl.
*A61B 5/00*   (2006.01)
*A61B 5/22*   (2006.01)

(52) U.S. Cl.
CPC .............. *A61B 5/4509* (2013.01); *A61B 5/22* (2013.01); *A61B 5/4836* (2013.01);
(Continued)

(58) Field of Classification Search
CPC ........ A61B 5/4509; A61B 5/22; A61B 5/4836
See application file for complete search history.

(56) References Cited

U.S. PATENT DOCUMENTS

| | | | |
|---|---|---|---|
| 5,931,780 A | 8/1999 | Giger et al. | |
| 6,205,348 B1* | 3/2001 | Giger ............. | A61B 6/583 600/407 |

(Continued)

FOREIGN PATENT DOCUMENTS

| | | |
|---|---|---|
| EP | 3851048 A1 | 7/2021 |
| JP | H09-508813 A | 9/1997 |

(Continued)

OTHER PUBLICATIONS

Lopez et al., A mechanical model for predicting the probability of osteoporotic hip fractures based in DXA measurements and finite element simulation, BioMedical Engineering OnLine 2012, 11:84; http://www.biomedical-engineering-online.com/content/11/1/84 (Year: 2012).*

(Continued)

*Primary Examiner* — Hugh Maupin
(74) *Attorney, Agent, or Firm* — SOLARIS Intellectual Property Group, PLLC

(57) ABSTRACT

A motor organ disease prediction device includes at least one processor, in which the processor derives a bone mineral density of a target bone among bones included in a subject including a bone part and a soft part, a muscle mass around the target bone, shape information representing a shape of the target bone, and shape information representing a shape of a bone adjacent to the target bone from a first radiation image and a second radiation image acquired by imaging the subject by radiation having different energy distributions. The processor derives a probability of occurrence of a motor organ disease relating to the target bone from the bone mineral density of the target bone, the muscle mass around the target bone, the shape information of the target bone, and the shape information of the bone adjacent to the target bone.

10 Claims, 17 Drawing Sheets

(52) U.S. Cl.
CPC .......... *A61B 5/7264* (2013.01); *A61B 5/7275* (2013.01); *A61B 5/743* (2013.01)

(56) References Cited

U.S. PATENT DOCUMENTS

| | | | | |
|---|---|---|---|---|
| 6,570,955 | B1* | 5/2003 | Siffert | G01N 23/04 |
| | | | | 378/207 |
| 7,901,873 | B2* | 3/2011 | Nicholson | G01R 33/465 |
| | | | | 435/25 |
| 2004/0062358 | A1 | 4/2004 | Lang et al. | |
| 2004/0077088 | A1* | 4/2004 | Charles, Jr. | A61B 6/032 |
| | | | | 435/455 |
| 2004/0101086 | A1* | 5/2004 | Sabol | A61B 6/4241 |
| | | | | 378/4 |
| 2004/0190679 | A1* | 9/2004 | Waggener | A61B 6/583 |
| | | | | 378/54 |
| 2005/0037515 | A1* | 2/2005 | Nicholson | G01R 33/465 |
| | | | | 436/173 |
| 2010/0135549 | A1 | 6/2010 | Pettersen et al. | |
| 2011/0036360 | A1* | 2/2011 | Lang | A61B 6/4423 |
| | | | | 128/898 |
| 2011/0142307 | A1 | 6/2011 | Ghosh et al. | |
| 2011/0243416 | A1 | 10/2011 | Gregory et al. | |
| 2014/0086383 | A1* | 3/2014 | Huwer | A61B 6/5211 |
| | | | | 378/5 |
| 2016/0015347 | A1* | 1/2016 | Bregman-Amitai | |
| | | | | G06T 7/0012 |
| | | | | 382/131 |
| 2021/0369224 | A1 | 12/2021 | Okano et al. | |
| 2022/0087533 | A1* | 3/2022 | El-Sallam | A61B 5/7267 |
| 2023/0129957 | A1* | 4/2023 | Udupa | A61B 6/5217 |
| | | | | 382/131 |

FOREIGN PATENT DOCUMENTS

| | | |
|---|---|---|
| JP | 2004-522465 A | 7/2004 |
| JP | 2010-522592 A | 7/2010 |
| JP | 2011-516988 A | 5/2011 |
| JP | 2016-220850 A | 12/2016 |
| JP | WO2020/054738 A1 | 10/2020 |
| WO | 2020/166561 A1 | 8/2020 |

OTHER PUBLICATIONS

English language translation of the following: Office action dated Jun. 4, 2024 from the JPO in a Japanese patent application No. 2021-019232 corresponding to the instant patent application. This office action translation is submitted now in order to supplement the understanding of the cited references which are being disclosed in the instant Information Disclosure Statement.

\* cited by examiner

MOTOR ORGAN DISEASE PREDICTION DEVICE, MOTOR ORGAN DISEASE PREDICTION METHOD, MOTOR ORGAN DISEASE PREDICTION PROGRAM, LEARNING DEVICE, LEARNING METHOD, LEARNING PROGRAM, AND LEARNED NEURAL NETWORK

CROSS REFERENCE TO RELATED APPLICATIONS

The present application claims priority under 35 U.S.C. § 119 to Japanese Patent Application No. 2021-019232 filed on Feb. 9, 2021. The above application is hereby expressly incorporated by reference, in its entirety, into the present application.

BACKGROUND

Technical Field

The present invention relates to a motor organ disease prediction device, a motor organ disease prediction method, a motor organ disease prediction program, a learning device, a learning method, a learning program, and a learned neural network.

Related Art

A disease, such as a fracture and a dislocation relating to motor organs, such as a bone, a joint, and a muscle, cause a patient to be bedridden. In particular, a dislocation of a hip joint and fractures of a femur and a vertebra are likely to result in the patient being bedridden. It is known that a 5-year survival rate in a case in which the patient is bedridden is lower than a 5-year survival rate for cancer. For this reason, various methods of evaluating a risk of a motor organ disease, especially the fracture risk, have been proposed.

For example, JP1997-508813A (JP-H09-508813A) proposes a method for acquiring bone mass and a bone structure from a radiation image and calculating a future fracture risk by using a neural network. In addition, JPWO2020-054738A proposes a method for estimating bone density from a radiation image by using a neural network and predicting a fracture by using a result of estimation and an operation expression representing a fracture probability. In addition, WO2020/166561A proposes a method for calculating a bone mineral density and a muscle mass for each pixel of a radiation image, calculating a statistical value relating to a subject based on the bone mineral density and the muscle mass, and evaluating the fracture risk based on the statistical value.

However, it is desirable to predict a motor organ disease with higher accuracy.

SUMMARY OF THE INVENTION

The present disclosure has been made in view of the above circumstances, and is to enable prediction of a motor organ disease with high accuracy.

A first aspect of the present disclosure relates to a motor organ disease prediction device comprising at least one processor, in which the processor derives a bone mineral density of a target bone among bones included in a subject including a bone part and a soft part, a muscle mass around the target bone, shape information representing a shape of the target bone, and shape information representing a shape of a bone adjacent to the target bone from a first radiation image and a second radiation image acquired by imaging the subject by radiation having different energy distributions, and derives a probability of occurrence of a motor organ disease relating to the target bone from the bone mineral density of the target bone, the muscle mass around the target bone, the shape information of the target bone, and the shape information of the bone adjacent to the target bone.

Note that in the motor organ disease prediction device according to the aspect of the present disclosure, the processor may function as a learned neural network which is machine-learned by using, as teacher data, the bone mineral density of the target bone among the bones included in a human body, the muscle mass around the target bone, the shape information representing the shape of the target bone, the shape information representing the shape of the bone adjacent to the target bone, and correct answer data representing the probability of occurrence of the motor organ disease relating to the target bone.

Note that in the motor organ disease prediction device according to the aspect of the present disclosure, the processor may display the derived probability of occurrence of the motor organ disease on a display.

In addition, in the motor organ disease prediction device according to the aspect of the present disclosure, the processor may display a graph representing a relationship between at least one of the bone mineral density or the muscle mass and the probability of occurrence of the motor organ disease, and may further display a plot representing the derived probability of occurrence of the motor organ disease and a plot representing a changed value the probability of occurrence or at least one of the bone mineral density or the muscle mass on the graph.

In addition, in the motor organ disease prediction device according to the aspect of the present disclosure, the changed value may be a target value of at least one of the bone mineral density or the muscle mass, or a target value of the probability of occurrence of the motor organ disease.

In addition, in the motor organ disease prediction device according to the aspect of the present disclosure, the processor may further display an option of a medical intervention for making at least one of the bone mineral density or the muscle mass reach the target value, or an option of a medical intervention for making the motor organ disease reach the target value.

In addition, in the motor organ disease prediction device according to the aspect of the present disclosure, the medical intervention may be an exercise method for training a muscle relating to the target bone.

In addition, in the motor organ disease prediction device according to the aspect of the present disclosure, the target bone may be a femur.

In addition, in the motor organ disease prediction device according to the aspect of the present disclosure, the target bone may be a vertebra.

In addition, in the motor organ disease prediction device according to the aspect of the present disclosure, the motor organ disease may be at least one of a fracture or a dislocation.

Another aspect of the present disclosure relates to a learning device comprising at least one processor, in which the processor machine-learns a neural network by using, as teacher data, a bone mineral density of a target bone among bones included in a human body, a muscle mass around the target bone, shape information representing a shape of the target bone, shape information representing a shape of the bone adjacent to the target bone, and correct answer data representing a probability of occurrence of a motor organ disease relating to the target bone to construct a learned neural network that outputs the probability of occurrence of the motor organ disease in a case in which the bone mineral density of the target bone, the muscle mass around the target bone, the shape information of the target bone, and the shape information of the bone adjacent to the target bone are input.

Still another aspect of the present disclosure relates to a motor organ disease prediction method comprising deriving a bone mineral density of a target bone among bones included in a subject including a bone part and a soft part, a muscle mass around the target bone, shape information representing a shape of the target bone, and shape information representing a shape of a bone adjacent to the target bone from a first radiation image and a second radiation image acquired by imaging the subject by radiation having different energy distributions, and deriving a probability of occurrence of a motor organ disease relating to the target bone from the bone mineral density of the target bone, the muscle mass around the target bone, the shape information of the target bone, and the shape information of the bone adjacent to the target bone.

Still another aspect of the present disclosure relates to a learning method comprising machine-learning a neural network by using, as teacher data, a bone mineral density of a target bone among bones included in a human body, a muscle mass around the target bone, shape information representing a shape of the target bone, shape information representing a shape of the bone adjacent to the target bone, and correct answer data representing a probability of occurrence of a motor organ disease relating to the target bone to construct a learned neural network that outputs the probability of occurrence of the motor organ disease in a case in which the bone mineral density of the target bone, the muscle mass around the target bone, the shape information of the target bone, and the shape information of the bone adjacent to the target bone are input.

Note that the motor organ disease prediction method and the learning method according to the aspects of the present disclosure may be provided as a program executed by a computer.

Still another aspect of the present disclosure relates to a learned neural network that outputs a probability of occurrence of a motor organ disease relating to a target bone among bones included in a human body in a case in which a bone mineral density of the target bone, muscle mass around the target bone, shape information representing a shape of the target bone, and shape information representing a shape of a bone adjacent to the target bone are input.

According to the present disclosure, it is possible to predict a motor organ disease with high accuracy.

DETAILED DESCRIPTION

Figure 1:
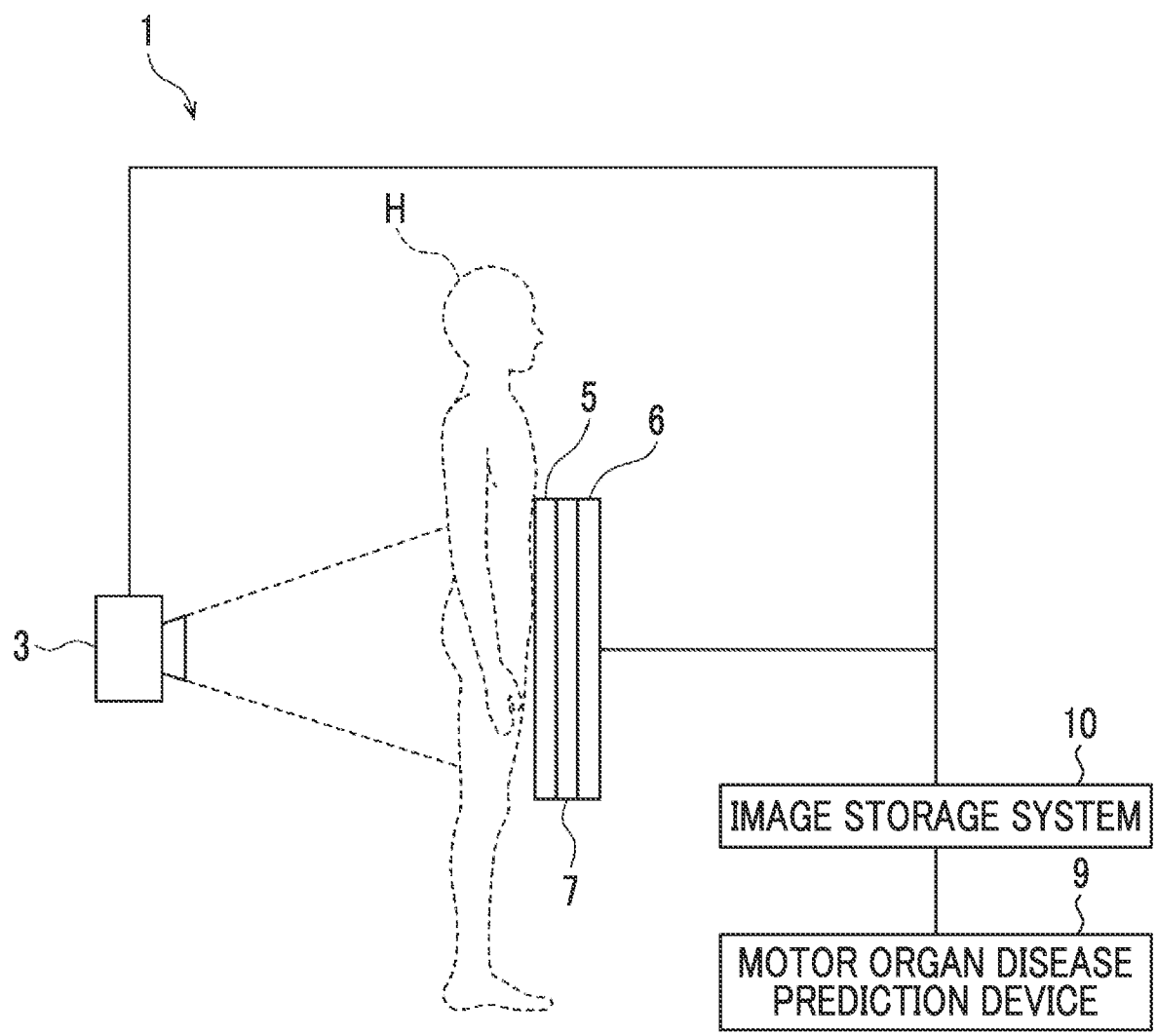
FIG. 1 is a schematic block diagram showing a configuration of a radiography system to which a motor organ disease prediction device and a learning device according to an embodiment of the present disclosure are applied.

In the following, an embodiment of the present disclosure will be described with reference to the drawings. FIG. 1 is a schematic block diagram showing a configuration of a radiography system to which a motor organ disease prediction device and a learning device according to the embodiment of the present disclosure are applied. As shown in FIG. 1, the radiography system according to the present embodiment comprises an imaging apparatus 1, and a motor organ disease prediction device and a learning device according to the present embodiment (hereinafter, may be represented by the motor organ disease prediction device) 10.

The imaging apparatus 1 is an imaging apparatus that performs energy subtraction by a so-called one-shot method for converting radiation, such as X-rays, emitted from a radiation source 3 and transmitted through a subject H into energy and irradiating a first radiation detector 5 and a second radiation detector 6 with the converted radiation. At the time of imaging, as shown in FIG. 1, the first radiation detector 5, a radiation energy conversion filter 7 made of a copper plate or the like, and the second radiation detector 6 are disposed in order from a side closest to the radiation source 3, and the radiation source 3 is driven. Note that the first and second radiation detectors 5 and 6 are closely attached to the radiation energy conversion filter 7.

As a result, in the first radiation detector 5, a first radiation image G1 of the subject H by low-energy radiation including so-called soft rays is acquired. In addition, in the second radiation detector 6, a second radiation image G2 of the subject H by high-energy radiation from which the soft rays are removed is acquired. The first radiation image G1 and the second radiation image G2 are input to the motor organ disease prediction device 10. Both the first radiation image G1 and the second radiation image G2 are front images including a periphery of a crotch of the subject H.

The first and second radiation detectors 5 and 6 can perform recording and reading-out of the radiation image repeatedly. A so-called direct-type radiation detector that directly receives emission of the radiation and generates an electric charge may be used, or a so-called indirect-type radiation detector that converts the radiation into visible light and then converts the visible light into an electric charge signal may be used. In addition, as a method for reading out a radiation image signal, it is desirable to use a so-called thin film transistor (TFT) readout method in which the radiation image signal is read out by turning a TFT switch on and off, or a so-called optical readout method in which the radiation image signal is read out by emission of read out light. However, other methods may also be used without being limited to these methods.

Note that the motor organ disease prediction device 10 is connected to an image storage system 9 via a network (not shown).

The image storage system 9 is a system that stores image data of the radiation image captured by the imaging apparatus 1. The image storage system 9 extracts an image corresponding to a request from the motor organ disease prediction device 10 from the stored radiation image and transmits the extracted image to a request source device. Specific examples of the image storage system 9 include picture archiving and communication systems (PACS).

Figure 2:
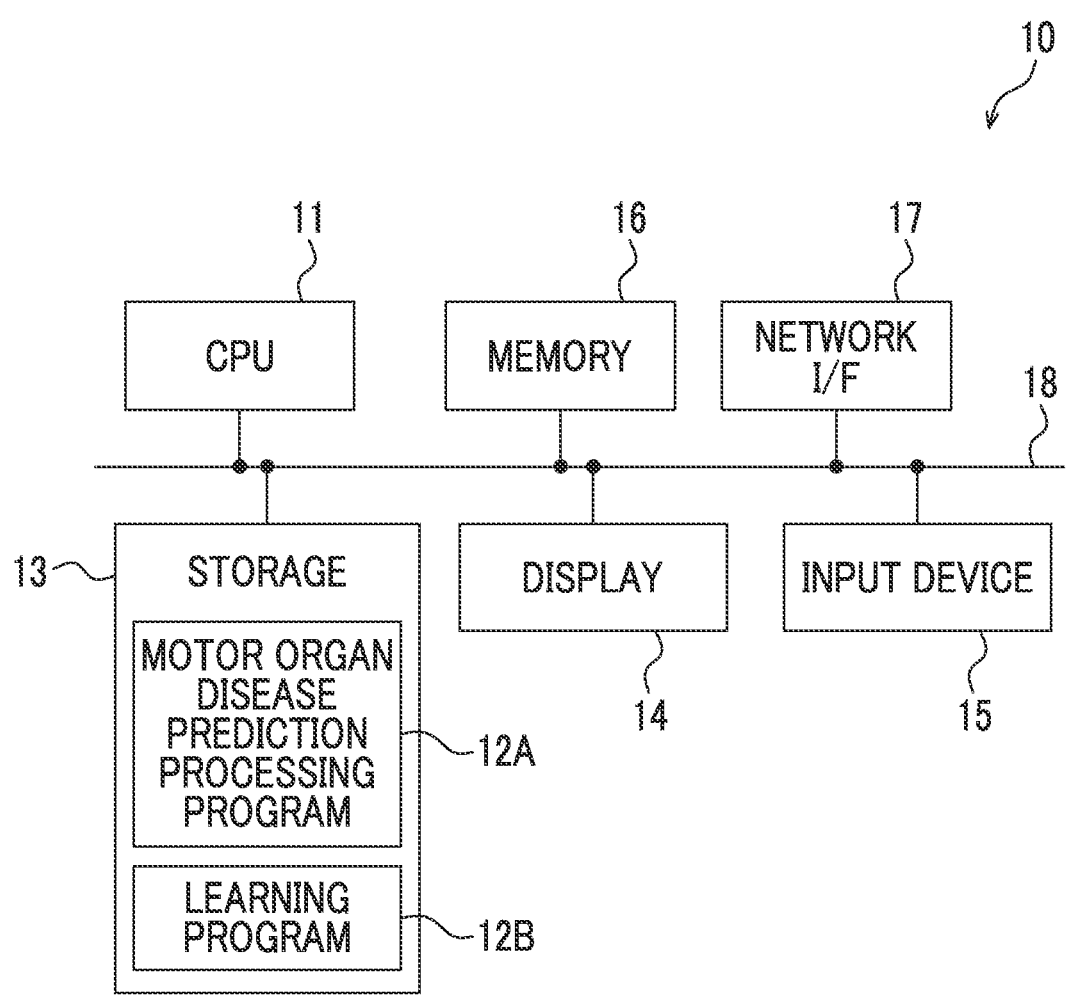
FIG. 2 is a diagram showing a schematic configuration of a motor organ disease prediction device and a learning device according to the embodiment of the present disclosure.

Then, the motor organ disease prediction device according to the present embodiment will be described. First, with reference to FIG. 2, a hardware configuration of the motor organ disease prediction device according to the present embodiment will be described. As shown in FIG. 2, the motor organ disease prediction device 10 is a computer, such as a workstation, a server computer, and a personal computer, and comprises a central processing unit (CPU) 11, a non-volatile storage 13, and a memory 16 as a transitory storage region. In addition, the motor organ disease prediction device 10 comprises a display 14, such as a liquid crystal display, an input device 15, such as a keyboard and a mouse, and a network interface (I/F) 17 connected to a network (not shown). The CPU 11, the storage 13, the display 14, the input device 15, the memory 16, and the network I/F 17 are connected to a bus 18. Note that the CPU 11 is an example of a processor according to the present disclosure.

The storage 13 is realized by a hard disk drive (HDD), a solid state drive (SSD), a flash memory, and the like. The storage 13 as a storage medium stores a motor organ disease prediction program 12A and a learning program 12B installed in the motor organ disease prediction device 10. The CPU 11 reads out the motor organ disease prediction program 12A and the learning program 12B from the storage 13, expands the motor organ disease prediction program 12A and the learning program 12B in the memory 16, and executes the expanded motor organ disease prediction program 12A and the expanded learning program 12B.

Note that the motor organ disease prediction program 12A and the learning program 12B are stored in a storage device of the server computer connected to the network or in a network storage in a state of being accessible from the outside, and are downloaded and installed in the computer that configures the motor organ disease prediction device 10 in response to the request. Alternatively, the motor organ disease prediction program 12A and the learning program 12B are distributed in a state of being recorded on a recording medium, such as a digital versatile disc (DVD) or a compact disc read only memory (CD-ROM), and are installed in the computer that configures the motor organ disease prediction device 10 from the recording medium.

Figure 3:
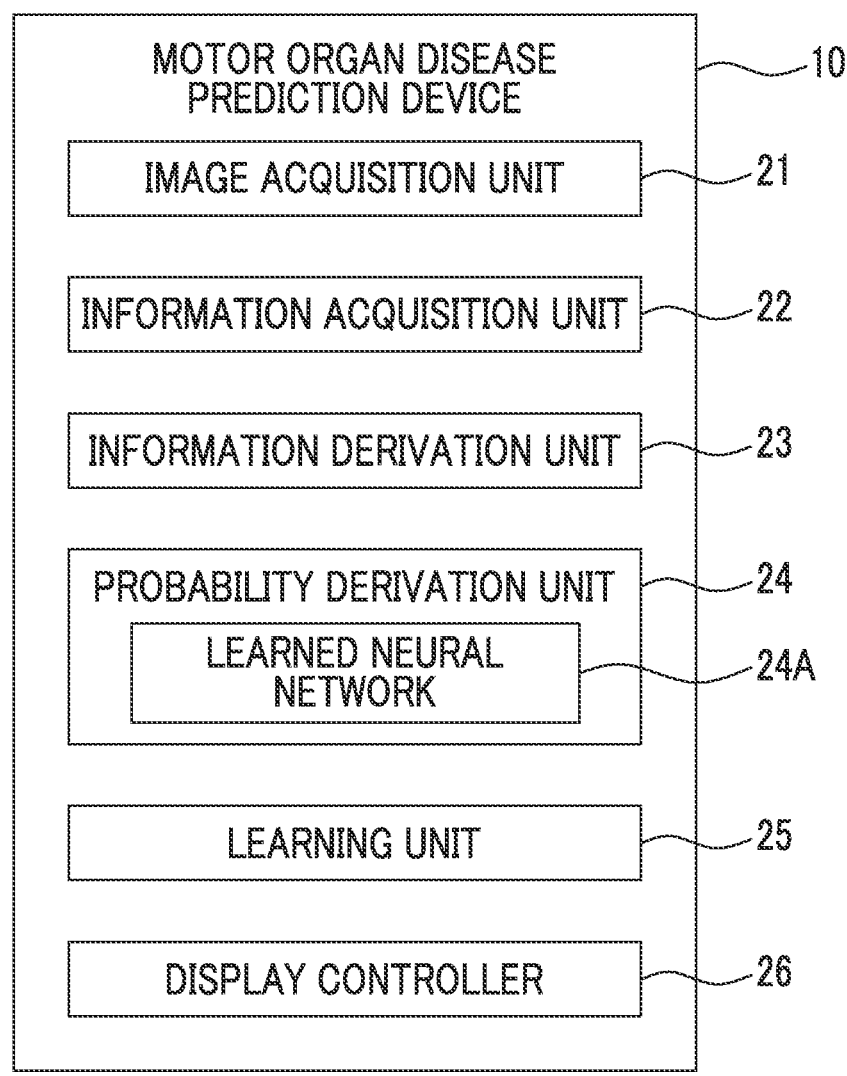
FIG. 3 is a diagram showing a functional configuration of the motor organ disease prediction device and the learning device according to the embodiment of the present disclosure.

Then, a functional configuration of the motor organ disease prediction device and the learning device according to the present embodiment will be described. FIG. 3 is a diagram showing a functional configuration of the motor organ disease prediction device and the learning device according to the present embodiment. As shown in FIG. 3, the motor organ disease prediction device 10 comprises an image acquisition unit 21, an information acquisition unit 22, an information derivation unit 23, a probability derivation unit 24, a learning unit 25, and a display controller 26. Further, the CPU 11 functions as the image acquisition unit 21, the information acquisition unit 22, the information derivation unit 23, the probability derivation unit 24, and the display controller 26 by executing the motor organ disease prediction program 12A, and further functions as a learned neural network 24A, which will be described below. In addition, the CPU 11 functions as the learning unit 25 by executing the learning program 12B.

The image acquisition unit 21 acquires the first radiation image G1 and the second radiation image G2 which are the front images of the periphery of the crotch of the subject H from the first and second radiation detectors 5 and 6 by causing the imaging apparatus 1 to image the subject H. In a case in which the first radiation image G1 and the second radiation image G2 are acquired, imaging conditions, such as an imaging dose, a tube voltage, a source image receptor distance (SID) which is a distance between the radiation source 3 and surfaces of the first and second radiation detectors 5 and 6, a source object distance (SOD) which is a distance between the radiation source 3 and a surface of the subject H, and the presence or absence of a scattered ray removal grid are set.

The SOD and the SID are used to calculate a body thickness distribution as described below. It is preferable that the SOD be acquired by, for example, a time of flight (TOF) camera. It is preferable that the SID be acquired by, for example, a potentiometer, an ultrasound range finder, a laser range finder, or the like.

The imaging conditions need only be set by input from the input device 15 by an operator. The set imaging conditions are stored in the storage 13. Note that in the present embodiment, the first and second radiation images G1 and G2 may be acquired by a program separate from the motor organ disease prediction program 12A and stored in the storage 13. In this case, the image acquisition unit 21 acquires the first and second radiation images G1 and G2 stored in the storage 13 by reading out the first and second radiation images G1 and G2 from the storage 13 for processing.

The information acquisition unit 22 acquires teacher data for learning a neural network, which will be described below, from the image storage system 9 via the network I/F 17.

The information derivation unit 23 derives a bone mineral density of a target bone among bones included in the subject H, a muscle mass around the target bone, shape information representing a shape of the target bone, and shape information representing a shape of a bone adjacent to the target bone. In the present embodiment, the target bone is a femur.

Figure 4:
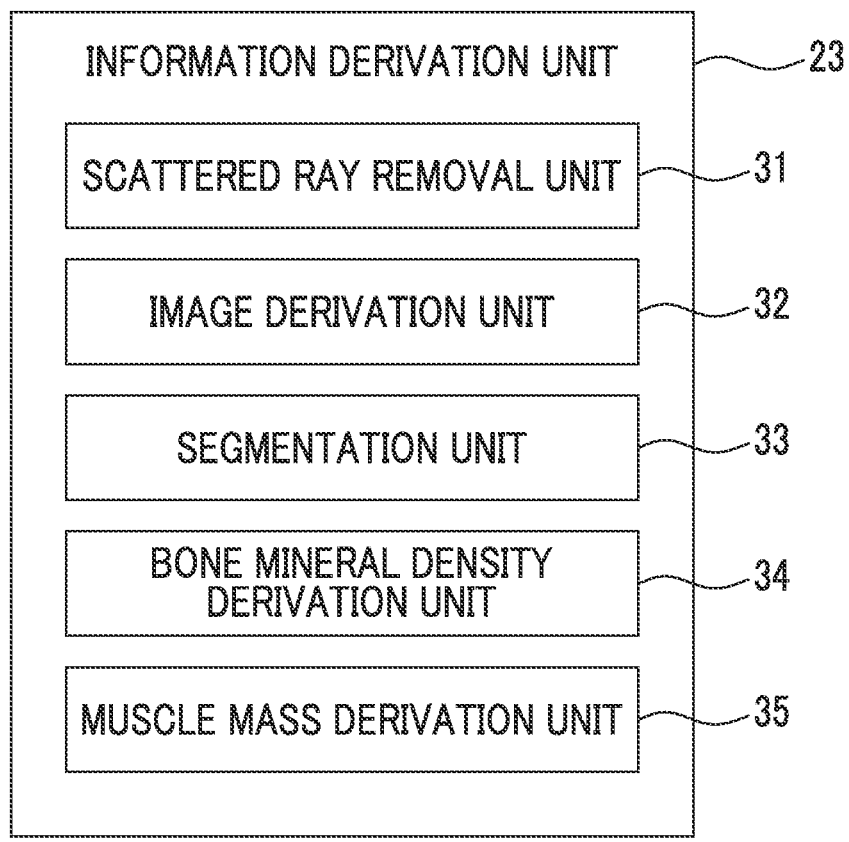
FIG. 4 is a diagram showing a functional configuration of an information derivation unit.

FIG. 4 is a schematic block diagram showing a configuration of the information derivation unit 23. As shown in FIG. 4, the information derivation unit 23 comprises a scattered ray removal unit 31, an image derivation unit 32, a segmentation unit 33, a bone mineral density derivation unit 34, and a muscle mass derivation unit 35. The CPU 11 functions as the scattered ray removal unit 31, the image derivation unit 32, the segmentation unit 33, the bone mineral density derivation unit 34, and the muscle mass derivation unit 35 by executing the motor organ disease prediction program 12A.

Here, each of the first radiation image G1 and the second radiation image G2 includes a scattered ray component based on the radiation scattered in the subject H in addition to a primary ray component of the radiation transmitted through the subject H. Therefore, the scattered ray removal unit 31 removes the scattered ray component from the first radiation image G1 and the second radiation image G2. For example, the scattered ray removal unit 31 may remove the scattered ray component from the first radiation image G1 and the second radiation image G2 by applying a method disclosed in JP2015-043959A. In a case in which a method disclosed in JP2015-043959A or the like is used, the derivation of the body thickness distribution of the subject H and the derivation of the scattered ray component for removing the scattered ray component are performed at the same time.

In the following, the removal of the scattered ray component from the first radiation image G1 will be described, but the removal of the scattered ray component from the second radiation image G2 can also be performed in the same manner. First, the scattered ray removal unit 31 acquires a virtual model K of the subject H having an initial body thickness distribution T0(x, y). The virtual model K is data virtually representing the subject H of which a body thickness depending on the initial body thickness distribution T0(x, y) is associated with a coordinate position of each pixel of the first radiation image G1. Note that the virtual model K of the subject H having the initial body thickness distribution T0(x, y) may be stored in the storage 13 in advance. In addition, a body thickness distribution T(x, y) of the subject H may be calculated based on the SID and the SOD included in the imaging conditions. In this case, the body thickness distribution can be obtained by subtracting the SOD from the SID.

Next, the scattered ray removal unit 31 generates, based on the virtual model K, an image obtained by composing an estimated primary ray image in which a primary ray image obtained by imaging the virtual model K is estimated and an estimated scattered ray image in which a scattered ray image obtained by imaging the virtual model K is estimated as an estimated image in which the first radiation image G1 obtained by imaging the subject H is estimated.

Next, the scattered ray removal unit 31 corrects the initial body thickness distribution T0(x, y) of the virtual model K such that a difference between the estimated image and the first radiation image G1 is small. The scattered ray removal unit 31 repeatedly performs the generation of the estimated image and the correction of the body thickness distribution until the difference between the estimated image and the first radiation image G1 satisfies a predetermined termination condition. The scattered ray removal unit 31 derives the body thickness distribution in a case in which the termination condition is satisfied as the body thickness distribution T(x, y) of the subject H. In addition, the scattered ray removal unit 31 removes the scattered ray component included in the first radiation image G1 by subtracting the scattered ray component in a case in which the termination condition is satisfied from the first radiation image G1.

Figure 5:
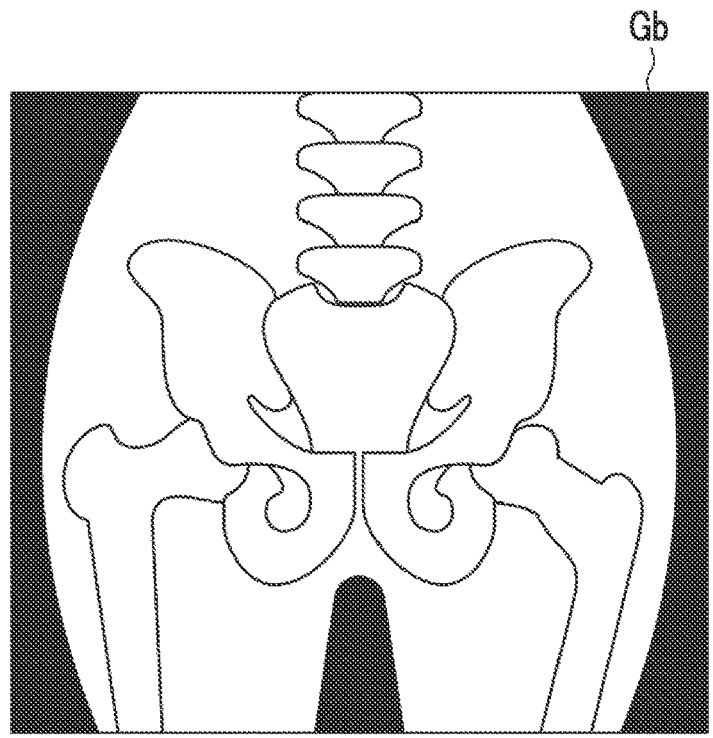
FIG. 5 is a diagram showing a bone part image.

The image derivation unit 32 performs energy subtraction processing to derive a bone part image Gb in which a bone part of the subject H is extracted and a soft part image Gs in which a soft part is extracted from the first and second radiation images G1 and G2. Note that in the first and second radiation images G1 and G2 in the subsequent processing, the scattered ray component is removed. In a case in which the bone part image Gb is derived, the image derivation unit 32 performs weighting subtraction between the corresponding pixels with respect to the first and second radiation images G1 and G2 as shown in Expression (1) to generate the bone part image Gb in which the bone part of the subject H included in each of the radiation images G1 and G2 is extracted, as shown in FIG. 5. In Expression (1), $\beta 1$ is a weighting coefficient. Note that a pixel value of each pixel in a bone region in the bone part image Gb is a bone part pixel value.

$$Gb(x,y)=G1(x,y)-\beta 1 \times G2(x,y) \tag{1}$$

Figure 6:
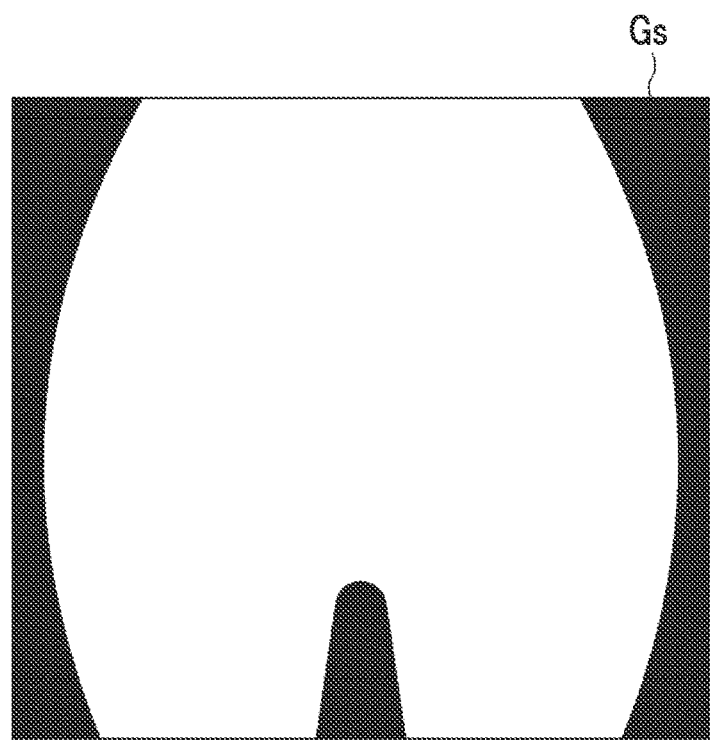
FIG. 6 is a diagram showing a soft part image.

On the other hand, in a case in which the soft part image Gs is derived, the image derivation unit 32 performs calculation, for example, weighting subtraction between the corresponding pixels with respect to the first and second radiation images G1 and G2 as shown in Expression (2) to generate the soft part image Gs in which only the soft part of the subject H included in each of the radiation images G1 and G2 is extracted, as shown in FIG. 6 (energy subtraction). In Expression (2), $\beta 2$ is a weighting coefficient.

$$Gs(x,y)=G1(x,y)-\beta 2 \times G2(x,y) \tag{2}$$

Note that the soft part image Gs shows a soft region due to a soft tissue of the subject H. In the present embodiment, the "soft tissue" of the subject H refers to a tissue other than a bone tissue, and specifically includes a muscle tissue, a fat tissue, blood, and water.

The segmentation unit 33 performs segmentation of the bone part image Gb into a femur region, a pelvis region, and a vertebra region, which are the target bones. The segmentation need only be performed by using an extraction model that is machine-learned to extract the femur, the pelvis, and the vertebra from the bone part image Gb, respectively. In addition, templates representing each of the femur, the pelvis, and the vertebra may be stored in the storage 13, and the segmentation may be performed by performing template matching between these templates and the bone part image Gb.

Figure 7:
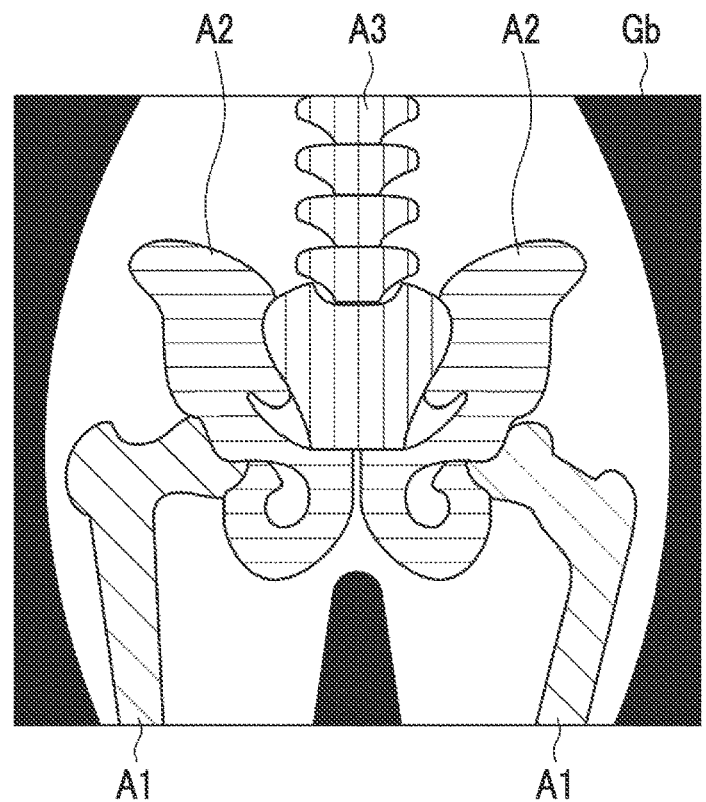
FIG. 7 is a diagram showing a result of segmentation.

FIG. 7 is a diagram showing a result of segmentation by the segmentation unit 33. As shown in FIG. 7, the bone region in the bone part image Gb is segmented into a region A1 of the femur, a region A2 of the pelvis, and a region A3 of the vertebra. Note that in FIG. 7, the result of segmentation is shown by giving different hatching to the region A1 of the femur, the region A2 of the pelvis, and the region A3 of the vertebra.

On the other hand, regarding the vertebra, the bone part image Gb includes only a sacral vertebra and a lumbar vertebra. The lumbar vertebra is anatomically classified as L5, L4, L3, L2, and L1 from a pelvis side to a neck. Therefore, it is preferable that the segmentation unit 33 perform the segmentation of the sacral vertebra and the five lumbar vertebrae into different regions.

Figure 8:
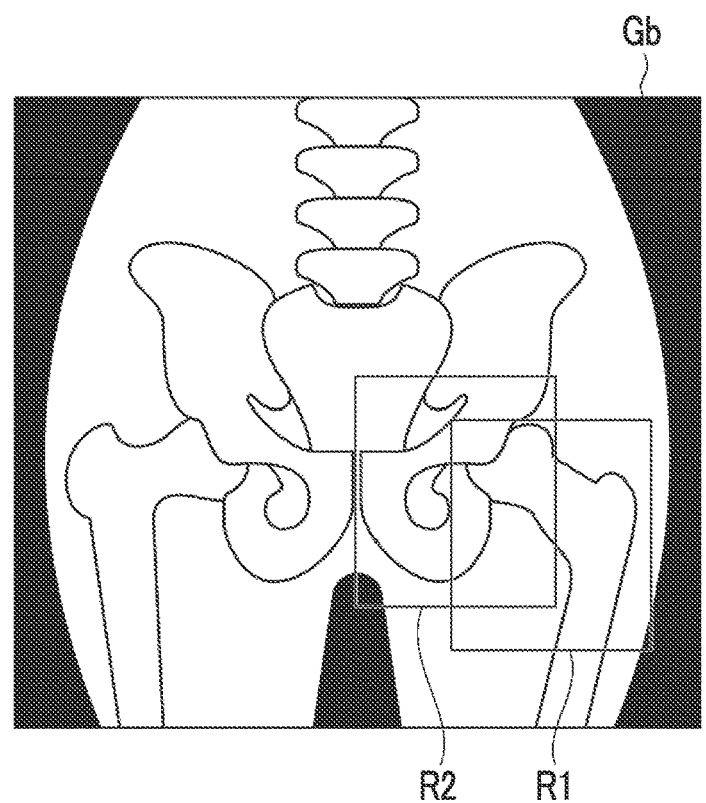
FIG. 8 is a diagram for describing setting of a region including a joint portion of a femur and a region including a joint portion of a pelvis.
Figure 9:
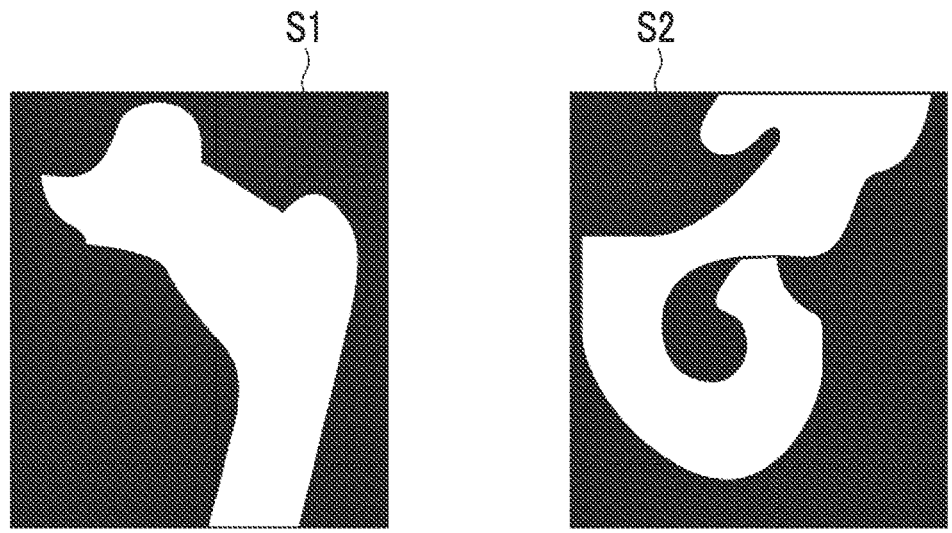
FIG. 9 is a diagram showing shape information of a target bone and shape information of a bone adjacent to the target bone.

In addition, as shown in FIG. 8, the segmentation unit 33 sets a region R1 including a joint portion of the femur and a region R2 including a joint portion of the pelvis in the bone part image Gb. Note that the regions R1 and R2 are set only on a left side of the subject H in FIG. 8, but the same is set on a right side. Further, by binarization of the region A1 of the femur in the region R1 and the other regions, shape information S1 representing the shape of the femur, which is the target bone, is derived as shown in FIG. 9. In addition, by binarization of the region A2 of the pelvis in the region R2 and the other regions, shape information S2 representing the shape of the pelvis, which is the bone part adjacent to the target bone, is derived as shown in FIG. 9.

The bone mineral density derivation unit 34 derives the bone mineral density for each pixel of the bone part image Gb. In the present embodiment, the bone mineral density derivation unit 34 derives a bone mineral density B by converting each pixel value of the bone part image Gb into the pixel value of the bone part image acquired under standard imaging conditions. More specifically, the bone mineral density derivation unit 34 derives the bone mineral density by correcting each pixel value of the bone part image Gb by using a correction coefficient acquired from a look-up table described below.

Here, the contrast between the soft part and the bone part in the radiation image is lower as the tube voltage in the radiation source 3 is higher and the energy of the radiation emitted from the radiation source 3 is higher. In addition, in a procedure of the radiation transmitted through the subject H, a low-energy component of the radiation is absorbed by the subject H, and beam hardening occurs in which the radiation energy is increased. The increase in the radiation energy due to the beam hardening is larger as the body thickness of the subject H is larger.

Figure 10:
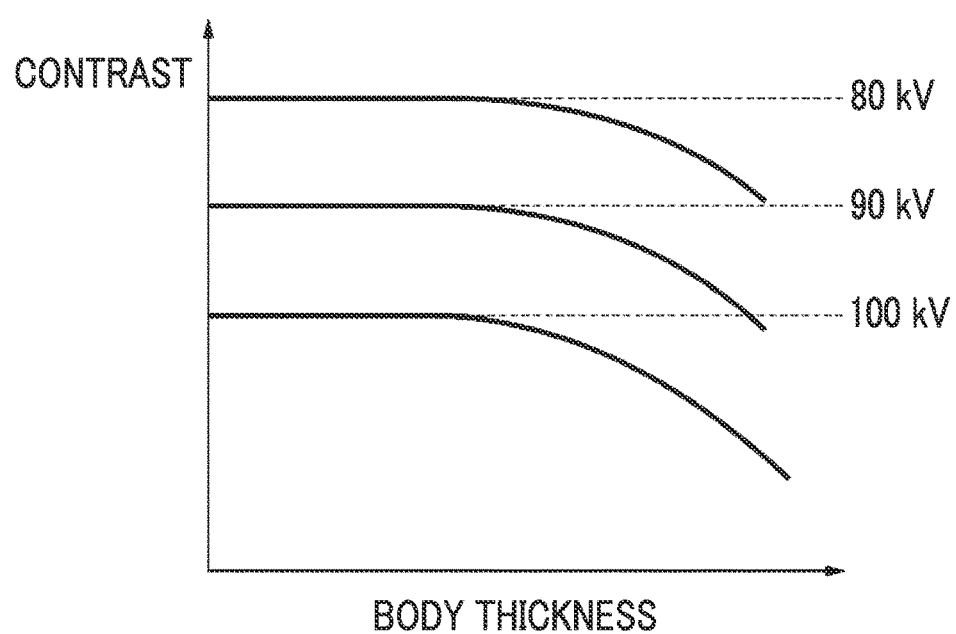
FIG. 10 is a diagram showing a relationship of a contrast between the bone part and the soft part with respect to a body thickness of a subject.

FIG. 10 is a diagram showing a relationship of the contrast between the bone part and the soft part with respect to the body thickness of the subject H. Note that FIG. 10 shows the relationship of the contrast between the bone part and the soft part with respect to the body thickness of the subject H at the three tube voltages of 80 kV, 90 kV, and 100 kV. As shown in FIG. 10, the contrast is lower as the tube voltage is higher. In addition, in a case in which the body thickness of the subject H exceeds a certain value, the contrast is lower as the body thickness is larger. Note that contrast between the bone part and the soft part is higher as the pixel value of the bone region in the bone part image Gb is larger. Therefore, the relationship shown in FIG. 10 shifts to a higher contrast side as the pixel value of the bone region in the bone part image Gb is increased.

In the present embodiment, the look-up table for acquiring the correction coefficient for correcting the difference in the contrast depending on the tube voltage at the time of imaging and the reduction in the contrast due to the influence of the beam hardening in the bone part image Gb is stored in the storage 13. The correction coefficient is the coefficient for correcting each pixel value of the bone part image Gb.

Figure 11:
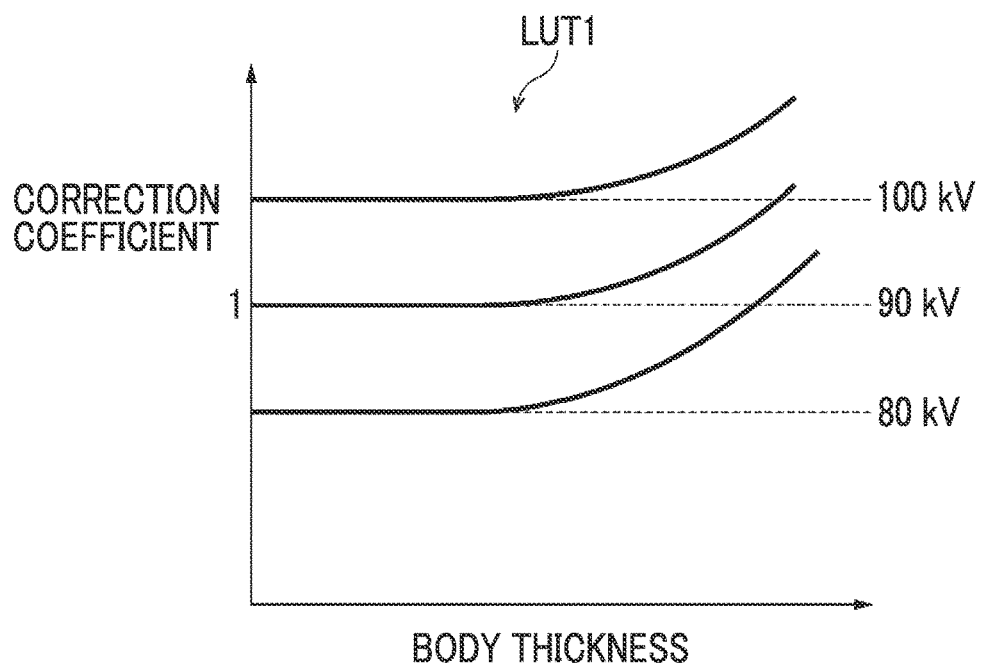
FIG. 11 is a diagram showing an example of a look-up table.

FIG. 11 is a diagram showing an example of the look-up table stored in the storage 13. In FIG. 11, a look-up table LUT1 in which the standard imaging condition is set to the tube voltage of 90 kV is shown. As shown in FIG. 11, in the look-up table LUT1, the correction coefficient is set to be larger as the tube voltage is higher and the body thickness of the subject H is larger. In the example shown in FIG. 11, since the standard imaging condition is the tube voltage of 90 kV, the correction coefficient is 1 in a case in which the tube voltage is 90 kV and the body thickness is 0. Note that although the look-up table LUT1 is shown in two dimensions in FIG. 11, the correction coefficient differs depending on the pixel value of the bone region. Therefore, the look-up table LUT1 is actually a three-dimensional table to which an axis representing the pixel value of the bone region is added.

The bone mineral density derivation unit 34 extracts the body thickness distribution T(x, y) of the subject H and a correction coefficient C0(x, y) for each pixel depending on the imaging conditions including a set value of the tube voltage stored in the storage 13 from the look-up table LUT1. Further, as shown in Expression (3), the bone mineral density derivation unit 34 multiplies each pixel (x, y) of the bone region in the bone part image Gb by the correction coefficient C0(x, y) to derive a bone mineral density B(x, y) (g/cm$^2$) for each pixel of the bone part image Gb. The bone mineral density B(x, y) derived in this way is acquired by imaging the subject H by the tube voltage of 90 kV, which is the standard imaging condition, and shows the pixel value of the bone region included in the radiation image from which the influence of the beam hardening is removed.

$$B(x,y)=C0(x,y)\times Gb(x,y) \qquad (3)$$

Note that in the present embodiment, the target bone is the femur. Therefore, the bone mineral density derivation unit 34 may derive the bone mineral density only for the region A1 of the femur in the bone part image Gb.

The muscle mass derivation unit 35 derives the muscle mass for each pixel in the soft region in the soft part image Gs based on the pixel value. As described above, the soft tissue includes the muscle tissue, the fat tissue, the blood, and the water. In the muscle mass derivation unit 35 according to the present embodiment, a tissue other than the fat tissue in the soft tissue is regarded as the muscle tissue. That is, in the muscle mass derivation unit 35 according to the present embodiment, a non-fat tissue including the blood and the water in the muscle tissue is handled as the muscle tissue.

Figure 12:
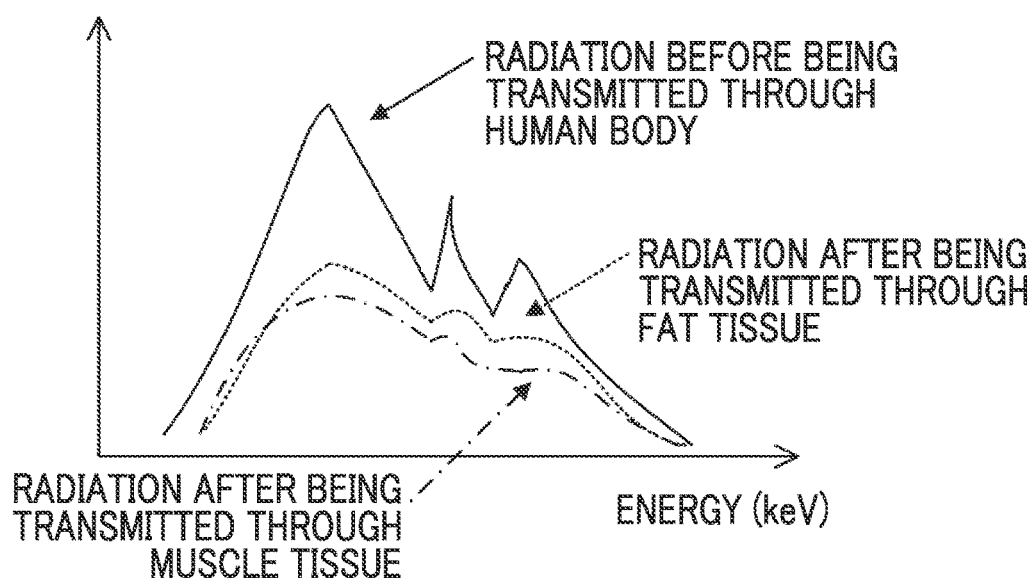
FIG. 12 is a diagram showing an example of energy spectra of radiation after being transmitted through a muscle tissue and radiation after being transmitted through a fat tissue.

The muscle mass derivation unit 35 separates the muscle and the fat from the soft part image Gs by using a difference in an energy characteristic between the muscle tissue and the fat tissue. As shown in FIG. 12, the dose of the radiation after being transmitted through the subject H is lower than the dose of the radiation before being incident on the subject H, which is a human body. In addition, since the energy absorbed by the muscle tissue and the energy absorbed by the fat tissue is different and attenuation coefficients are different, the energy spectra of the radiation after being transmitted through the muscle tissue and the radiation after being transmitted through the fat tissue in the radiation after being transmitted through the subject H are different. As shown in FIG. 12, the energy spectrum of the radiation transmitted through the subject H and emitted to each of the first radiation detector 5 and the second radiation detector 6 depends on a body composition of the subject H, specifically, a ratio between the muscle tissue and the fat tissue. Since the fat tissue is more likely to transmit the radiation than the muscle tissue, the dose of the radiation after being transmitted through the human body is smaller in a case in which the ratio of the muscle tissue is larger than the ratio of the fat tissue.

Therefore, the muscle mass derivation unit 35 separates the muscle and the fat from the soft part image Gs by using the difference in the energy characteristic between the muscle tissue and the fat tissue described above. That is, the muscle mass derivation unit 35 generates a muscle image and a fat image from the soft part image Gs. In addition, the muscle mass derivation unit 35 derives the muscle mass of each pixel based on the pixel value of the muscle image.

Note that a specific method by which the muscle mass derivation unit 35 separates the muscle and the fat from the soft part image Gs is not limited, but as an example, the muscle mass derivation unit 35 according to the present embodiment generates the muscle image from the soft part image Gs by Expression (4) and Expression (5). Specifically, first, the muscle mass derivation unit 35 derives a muscle ratio rm(x, y) at each pixel position (x, y) in the soft part image Gs by Expression (4). Note that in Expression (4), μm is a weighting coefficient depending on an attenuation coefficient of the muscle tissue, and μf is a weighting coefficient depending on an attenuation coefficient of the fat tissue. In addition, Δ(x, y) indicates a concentration difference distribution. The concentration difference distribution is a distribution of a concentration change on the image, which is seen from a concentration obtained by making the radiation reach the first radiation detector 5 and the second radiation detector 6 without transmitted through the subject H. The distribution of the concentration change on the image is calculated by subtracting the concentration of each pixel in the region of the subject H from the concentration in a blank region obtained by directly emitting the radiation in the soft part image Gs to the first radiation detector 5 and the second radiation detector 6.

$$rm(x,y) = \{\mu f - \Delta(x,y)/T(x,y)\}/(\mu f - \mu m) \quad (4)$$

Moreover, the muscle mass derivation unit 35 generates a muscle image Gm from the soft part image Gs by Expression (5). Note that x and y in Expression (5) are the coordinates of each pixel of the muscle image Gm.

$$Gm(x,y) = rm(x,y) \times Gs(x,y) \quad (5)$$

Further, as shown in Expression (6), the muscle mass derivation unit 35 derives the muscle mass M(x, y) (g/cm$^2$) for each pixel of the muscle image Gm by multiplying each pixel (x, y) of the muscle image Gm by a coefficient C1(x, y) representing a relationship between a predetermined pixel value and the muscle mass.

$$M(x,y) = C1(x,y) \times Gm(x,y) \quad (6)$$

Figure 13:
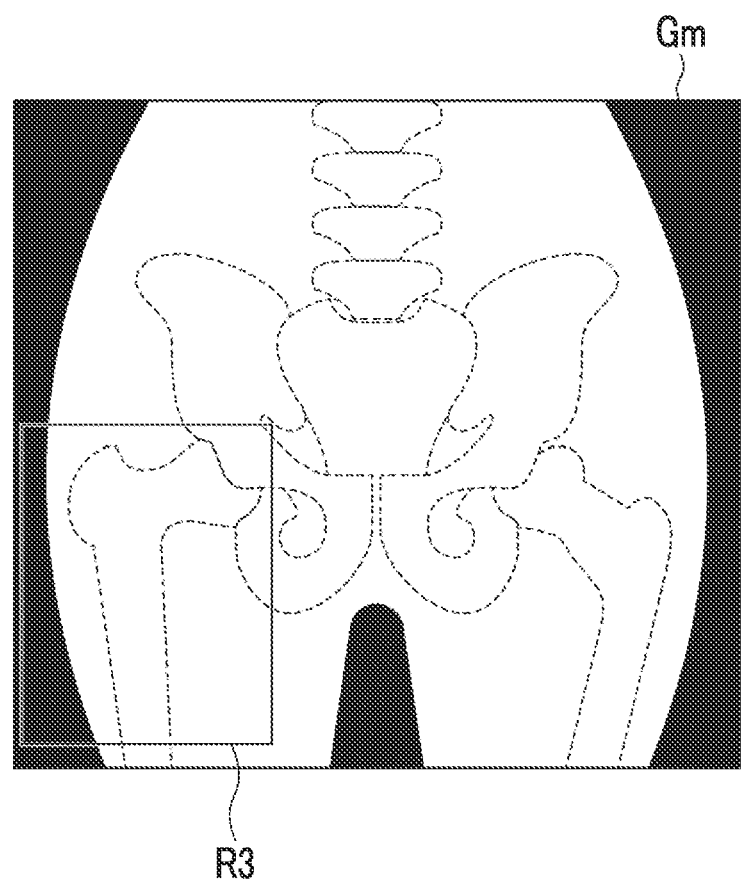
FIG. 13 is a diagram for describing setting of a region of a periphery of the femur in a muscle image.

Note that in the present embodiment, since the target bone is the femur, as shown in FIG. 13, the muscle mass M may be derived only in a region R3 of a periphery of the femur in the muscle image Gm.

In addition, the derivation of the muscle mass is not limited to the method described above, and for example, as disclosed in WO2020/166561A, the muscle mass may be obtained based on the body thickness distribution and the pixel value of the soft part image Gs.

The probability derivation unit 24 derives a probability of occurrence of the motor organ disease relating to the target bone from the bone mineral density of the target bone, the muscle mass around the target bone, the shape information of the target bone, and the shape information of the bone adjacent to the target bone. Therefore, in a case in which the bone mineral density of the target bone, the muscle mass around the target bone, the shape information of the target bone, and the shape information of the bone adjacent to the target bone are input, the probability derivation unit 24 derives the probability of occurrence of the motor organ disease relating to the target bone by using the learned neural network 24A that outputs the probability of occurrence of the motor organ disease relating to the target bone.

The learning unit 25 constructs the learned neural network 24A by machine-learning the neural network by using, as teacher data, the bone mineral density of the target bone among the bones included in a human body, the muscle mass around the target bone, the shape information representing the shape of the target bone, the shape information representing the shape of the bone adjacent to the target bone, and correct answer data representing the probability of occurrence of the motor organ disease relating to the target bone.

Examples of the neural network include a simple perceptron, a multi-layer perceptron, a deep neural network, a convolutional neural network, a deep belief network, a recurrent neural network, and a stochastic neural network. In the present embodiment, the convolutional neural network is used as the neural network.

Figure 14:
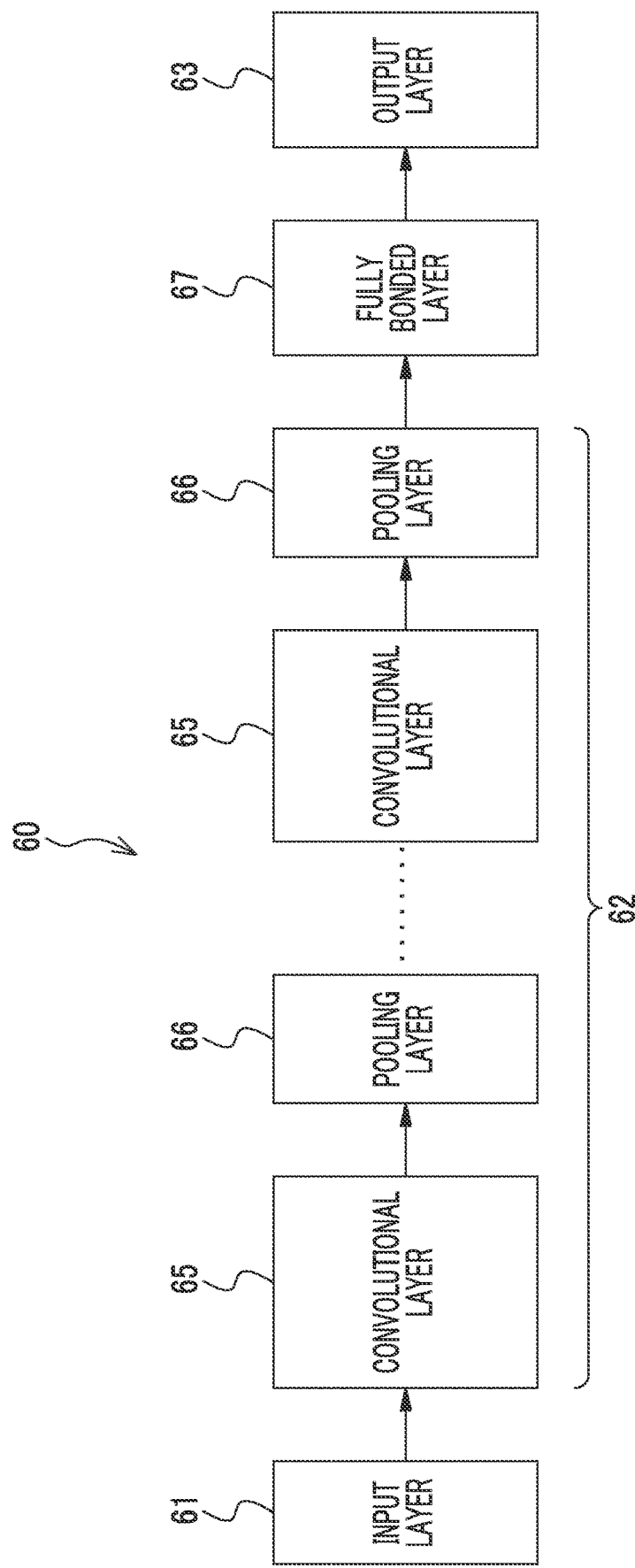
FIG. 14 is a diagram showing a schematic configuration of a neural network used in the present embodiment.

FIG. 14 is a diagram showing the neural network used in the present embodiment. As shown in FIG. 14, a neural network 60 comprises an input layer 61, an interlayer 62, and an output layer 63. The interlayer 62 comprises, for example, a plurality of convolutional layers 65, a plurality of pooling layers 66, and a fully bonded layer 67. In the neural network 60, the fully bonded layer 67 is present in front of the output layer 63. Further, in the neural network 60, the convolutional layer 65 and the pooling layer 66 are alternately disposed between the input layer 61 and the fully bonded layer 67.

Note that a configuration of the neural network 60 is not limited to the example of FIG. 14. For example, the neural network 60 may comprise one convolutional layer 65 and one pooling layer 66 between the input layer 61 and the fully bonded layer 67.

Figure 15:
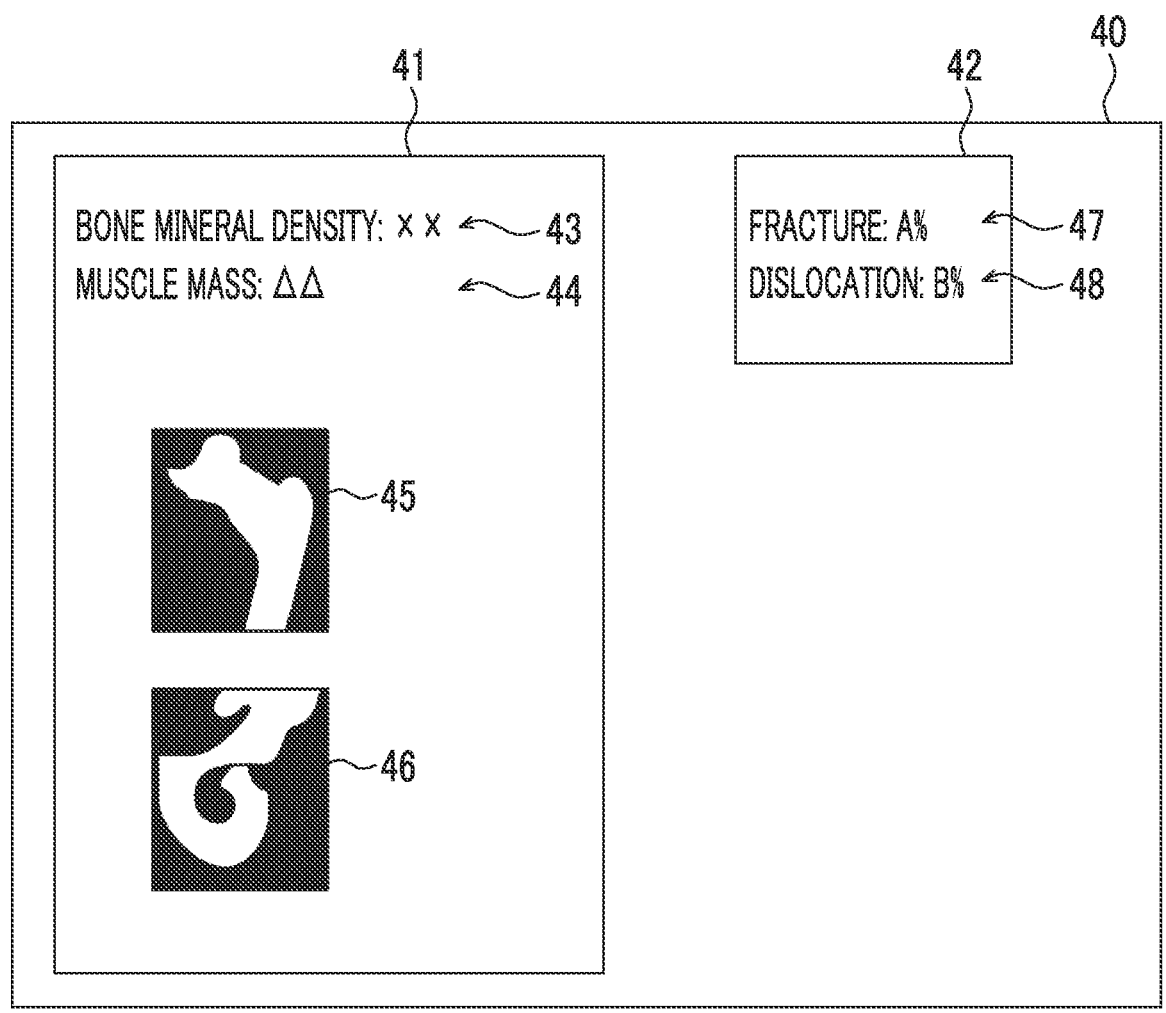
FIG. 15 is a diagram showing teacher data.

FIG. 15 is a diagram showing an example of teacher data used for learning the neural network. As shown in FIG. 15, teacher data 40 consists of learning data 41 and correct answer data 42. The learning data 41 consists of the bone mineral density of the target bone (bone mineral density) 43, the muscle mass around the target bone (muscle mass) 44, shape information 45 of the target bone, and shape information 46 of the bone adjacent to the target bone. The correct answer data 42 consists of a probability of occurrence of a fracture 47 and a probability of occurrence of a dislocation (hip joint dislocation) 48 as the motor organ disease.

Regarding a plurality of the patients, the teacher data is derived by recording statistics of the bone mineral density, the muscle mass, shape information of the target bone, and the shape information of the bone adjacent to the target bone of the patient in a case in which the fracture and the dislocation occur and stored in the image storage system 9. The probability of occurrence of the fracture and the dislocation, which is the correct answer data 42 in the teacher data 40 can be calculated by obtaining the number of cases of occurrence of the fracture and the dislocation after a predetermined number of years (for example, 1 year, 2 years, or 5 years) elapses, and dividing the obtained number of cases by the number of patients, regarding the plurality of patients who has the bone mineral density, the muscle mass, the shape information of the target bone, and the shape information of the bone adjacent to the target bone similar to each other.

Figure 16:
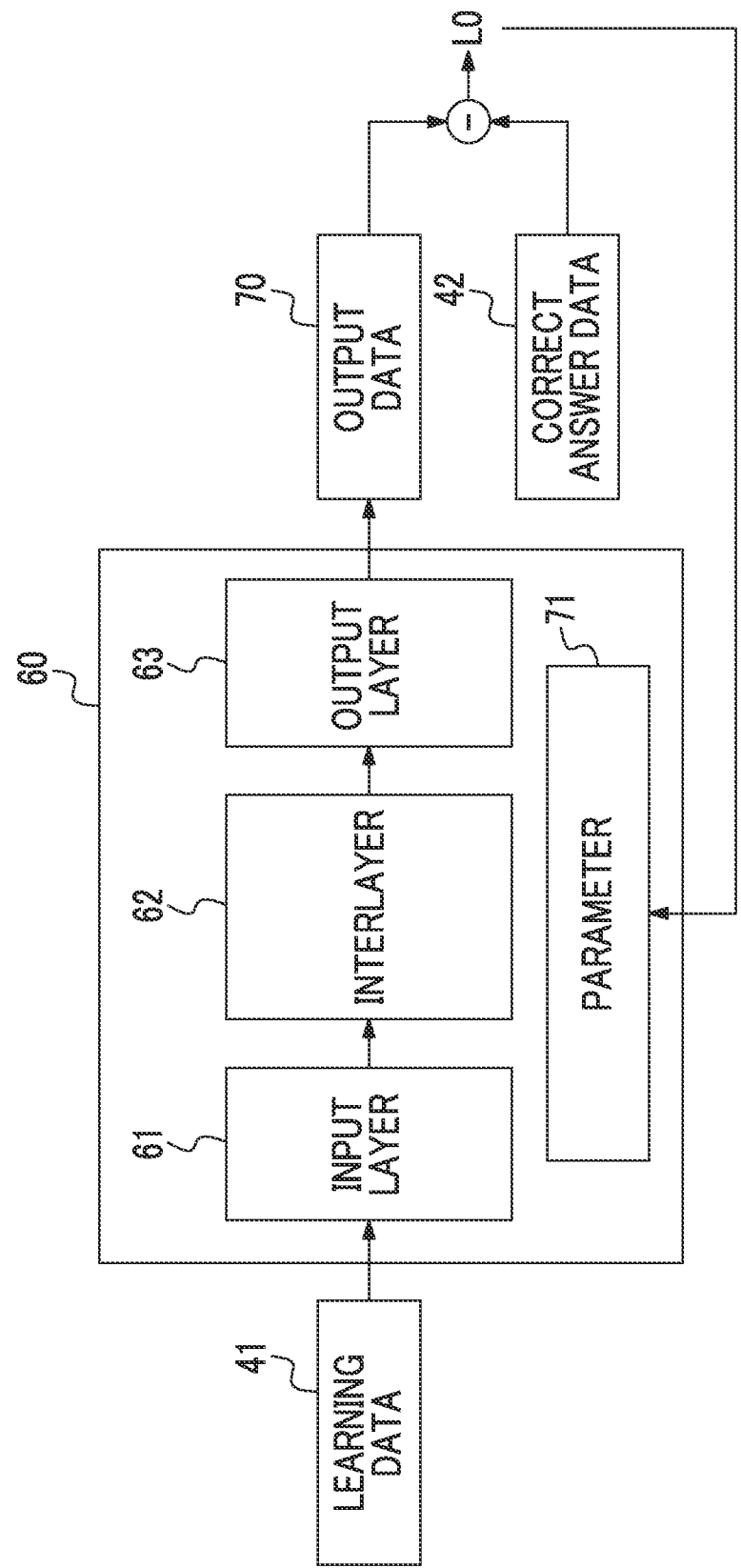
FIG. 16 is a diagram for describing learning of the neural network.

The learning unit 25 learns the neural network by using a large amount of the teacher data 40. FIG. 16 is a diagram for describing learning of the neural network 60. In a case in which the neural network 60 is learned, the learning unit 25 inputs the learning data 41 to the input layer 61 of the neural network 60. Further, the learning unit 25 outputs the probability of occurrence of the motor organ disease, that is, the fracture and the dislocation as output data 70 from the output layer 63 of the neural network 60. Further, the learning unit 25 derives a difference between the output data 70 and the probability of occurrence included in the correct answer data 42 as a loss L0.

The learning unit 25 learns the neural network 60 based on the loss L0. Specifically, the learning unit 25 adjusts a kernel coefficient in the convolutional layer 65, a weight of the bond between the layers, a weight of the bond in the fully bonded layer 67, and the like (hereinafter referred to as a parameter 71) such that the loss L0 is reduced. For example, an error backpropagation method can be used as a method for adjusting the parameter 71. The learning unit 25 repeats the adjustment of the parameter 71 until the loss L0 is equal to or smaller than a predetermined threshold value. As a result, in a case in which the bone mineral density, the muscle mass, the shape information of the target bone, and the shape information of the bone adjacent to the target bone are input, the parameter 71 is adjusted such that a more accurate probability of the fracture and the dislocation is output, and the learned neural network 24A is constructed. The constructed learned neural network 24A is stored in the storage 13.

In a case in which the bone mineral density, the muscle mass, the shape information of the target bone, and the shape information of the bone adjacent to the target bone of the patient are input to the learned neural network 24A constructed in this way, the learned neural network 24A outputs the probability of occurrence of the fracture of the femur and the probability of occurrence of the hip joint dislocation regarding the patient.

Note that the bone mineral density and the muscle mass included in the learning data 41 are input to the neural network 60 at the time of the learning. For example, regarding the bone mineral density, a representative value of the bone mineral density in the femur region in the region R1 including the joint portion of the femur shown in FIG. 8 is input. As the representative value, an average value, a maximum value, a minimum value, an intermediate value, or the like can be used. In addition, all the values of the bone mineral density in the femur region in the region R1 may be input, or the bone mineral density at a plurality of predetermined points in the femur region in the region R1 may be input. Note that in a case in which the probability derivation unit 24 derives the probability of occurrence of the motor organ disease, the same bone mineral density as in a case of learning the neural network 60 is input to the learned neural network 24A.

In addition, regarding the muscle mass, a representative value of the muscle mass around the femur in the region R3 including the joint portion of the femur shown in FIG. 13 is input to the neural network 60 at the time of the learning. As the representative value, an average value, a maximum value, a minimum value, an intermediate value, or the like can be used. In addition, all the values of the muscle mass in the region R3 around the femur may be input, or the muscle mass at a plurality of predetermined points in the region R3 may be input. In this case, in a case in which the probability derivation unit 24 derives the probability of occurrence of the motor organ disease, the same muscle mass as in a case of learning the neural network 60 is input to the learned neural network 24A.

Regarding the shape information of the target bone and the shape information of the bone adjacent to the target bone, a binary image representing the shape information is input to the learned neural network 24A.

The display controller 26 displays the probability of occurrence of the motor organ disease derived by the probability derivation unit 24 on the display 14.

Figure 17:
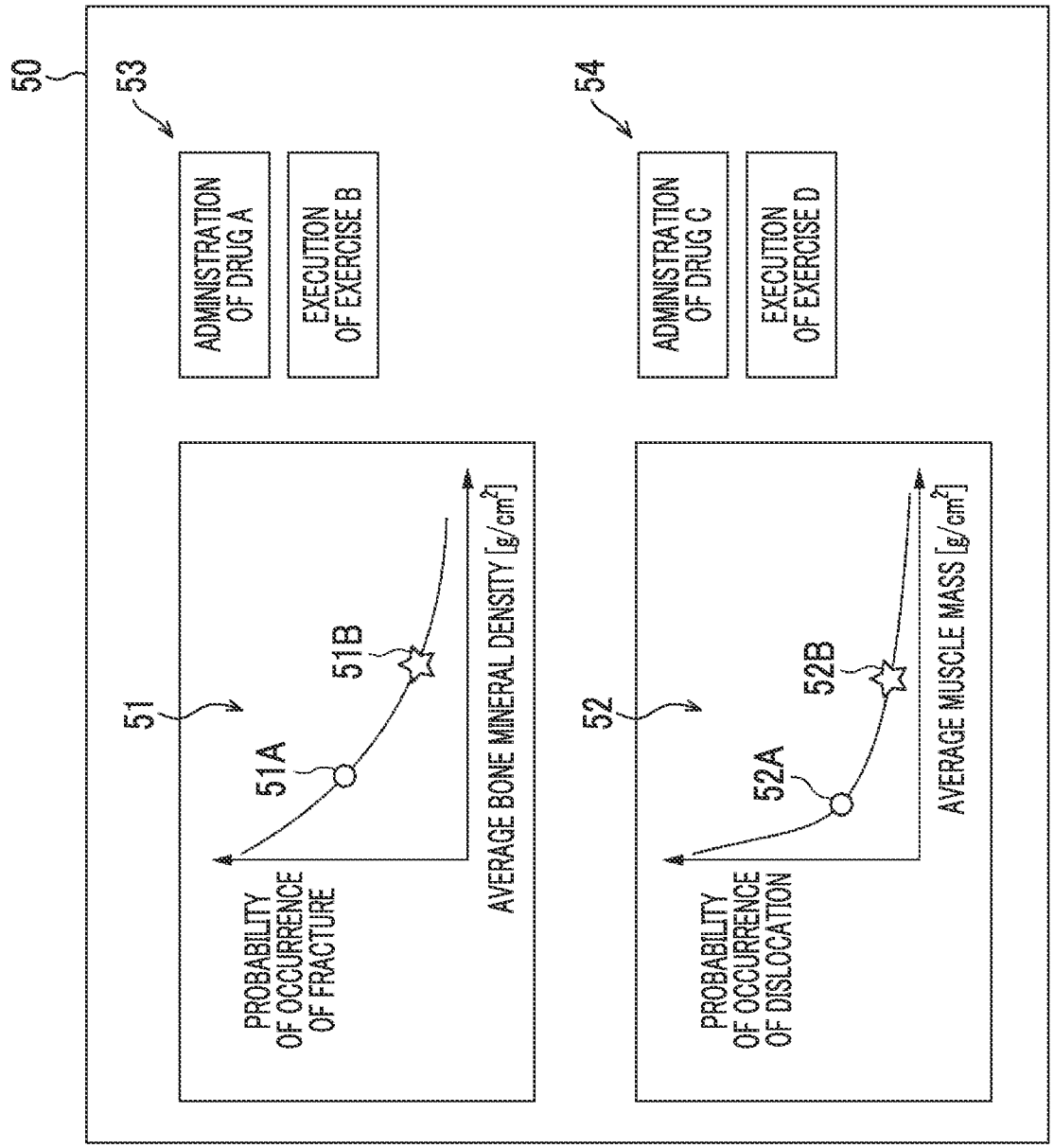
FIG. 17 is a diagram showing a display screen.

FIG. 17 is a diagram showing a display screen of the probability of occurrence of the motor organ disease. As shown in FIG. 17, on a display screen 50, a first graph 51 representing a relationship between an average bone mineral density and the probability of occurrence of the fracture, and a second graph 52 representing a relationship between an average muscle mass and the probability of occurrence of the dislocation are displayed. In the first graph 51, a lateral axis indicates the average bone mineral density and a vertical axis indicates the probability of occurrence of the fracture, and the probability of occurrence of the fracture is higher as the average bone mineral density is smaller. In addition, in the first graph 51, a white circle plot 51A representing a current probability of occurrence of the fracture derived by the probability derivation unit 24 and a star-marked plot 51B representing a target value of the probability of occurrence are given. The target value is the probability of halving the probability of occurrence of the motor organ disease derived by the probability derivation unit 24.

In addition, on a right side of the first graph 51, options 53 of the medical intervention for making the bone mineral density reach the target value are displayed. In FIG. 17, "administration of drug A" and "execution of exercise B" are displayed as the options. The drug A is a name of a drug for making the bone mineral density reach the target value. The exercise B is an exercise for training the muscle relating to the target bone. Specifically, the exercise B is a squat for training the muscle around the hip joint.

In addition, in the second graph 52, a lateral axis indicates the average muscle mass and a vertical axis indicates the probability of occurrence of the dislocation, and the probability of occurrence of the dislocation is higher as the average muscle mass is smaller. In addition, in the second graph 52, a white circle plot 52A representing a current probability of occurrence of the dislocation and a star-marked plot 52B representing a target probability of occurrence in a case in which the muscle mass is changed are given. The target value is the probability of halving the probability of occurrence of the motor organ disease derived by the probability derivation unit 24.

In addition, on a right side of the second graph 52, options 54 of the medical intervention for making the muscle mass reach the target value are displayed. In FIG. 17, "administration of drug C" and "execution of exercise D" are displayed as the options. The drug C is a name of a drug for making the muscle mass reach the target value. The exercise D is also an exercise for training the muscle relating to the target bone. Specifically, the exercise B is a squat for training the muscle around the hip joint.

Note that in the present embodiment, depending on patient information, such as age, gender, height, weight, and fracture history of the patient who is the subject H, a table in which a relationship between the average bone mineral density and/or the average muscle mass and the probability of occurrence of the motor organ disease is defined is stored in the storage 13. With reference to this table, the display controller 26 displays the first graph 51 and the second graph 52.

In addition, in addition to or instead of the first graph 51 and the second graph 52, a graph representing the probability of occurrence of the fracture with respect to the average muscle mass and a graph representing the probability of occurrence of the dislocation with respect to the average bone mineral density may be displayed.

Figure 18:
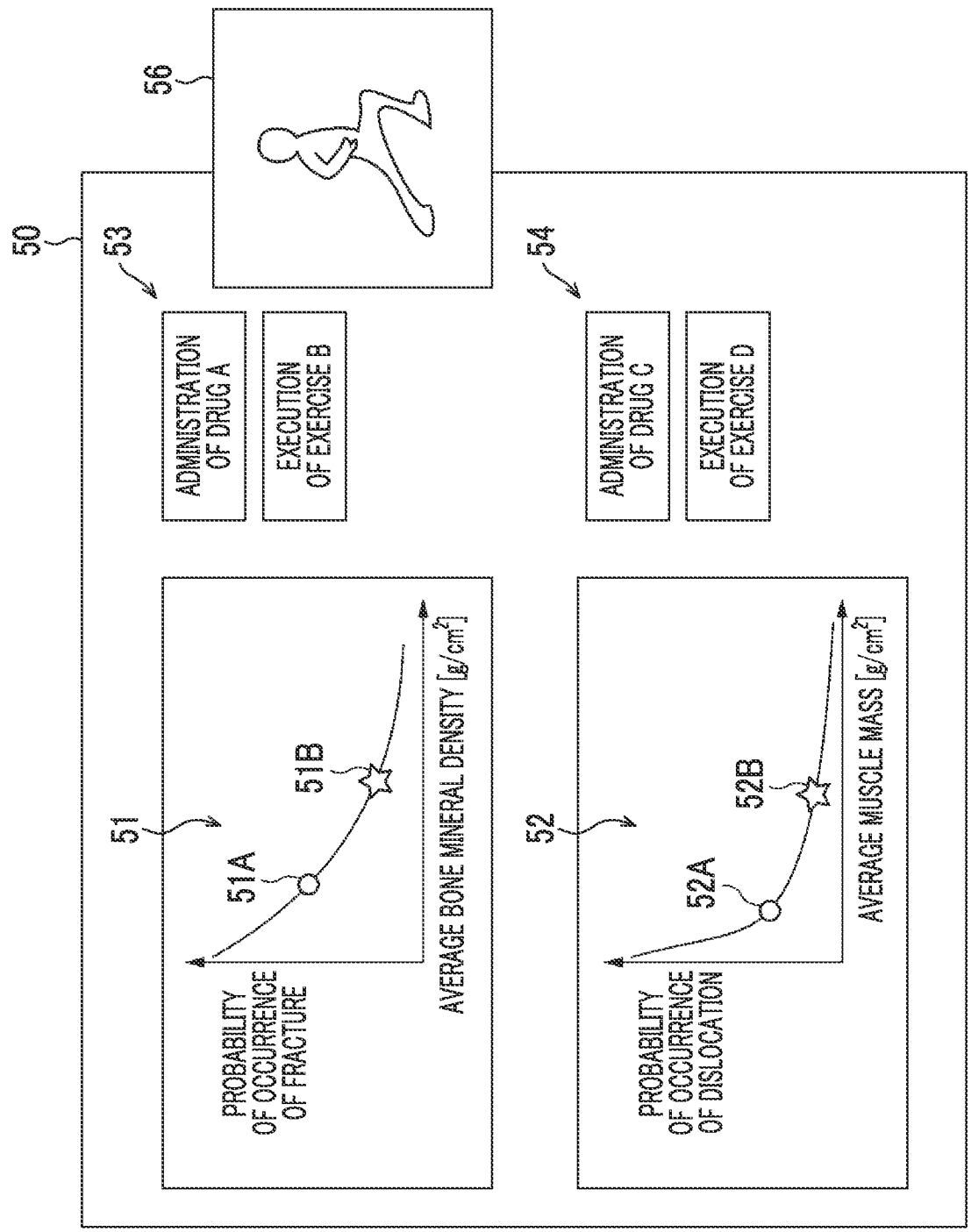
FIG. 18 is a diagram showing the display screen.

In addition, the display controller 26 may display the display screen 50 to be selectable by clicking "execution of exercise B" and "execution of exercise D" displayed in the options 53 and 54. In this case, in a case in which the operator selects "execution of exercise B" or "execution of exercise D", the display controller 26 may display a motion picture of the exercise for training the muscle relating to the target bone by a separate window 56 as shown in FIG. 18.

Figure 19:
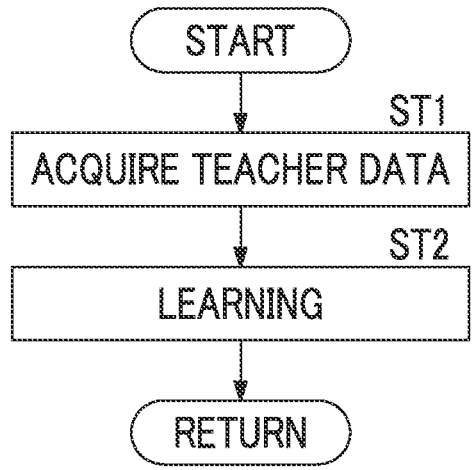
FIG. 19 is a flowchart of learning processing performed in the present embodiment.

Then, processing performed in the present embodiment will be described. FIG. 19 is a flowchart showing learning processing performed in the present embodiment. First, the information acquisition unit 22 acquires the teacher data from the image storage system 9 (step ST1), and the learning unit 25 inputs the learning data 41 included in the teacher data 40 to the neural network 60 to output the probability of occurrence of the motor organ disease and learns the neural network 60 by using the loss L0 based on the difference from the correct answer data 42 (step ST2), and the processing returns to step ST1. Further, the learning unit 25 repeats the processing of steps ST1 and ST2 until the loss L0 reaches the predetermined threshold value, and terminates the learning. Note that the learning unit 25 may terminate the learning by repeating the learning a predetermined number of times. As a result, the learning unit 25 constructs the learned neural network 24A.

Figure 20:
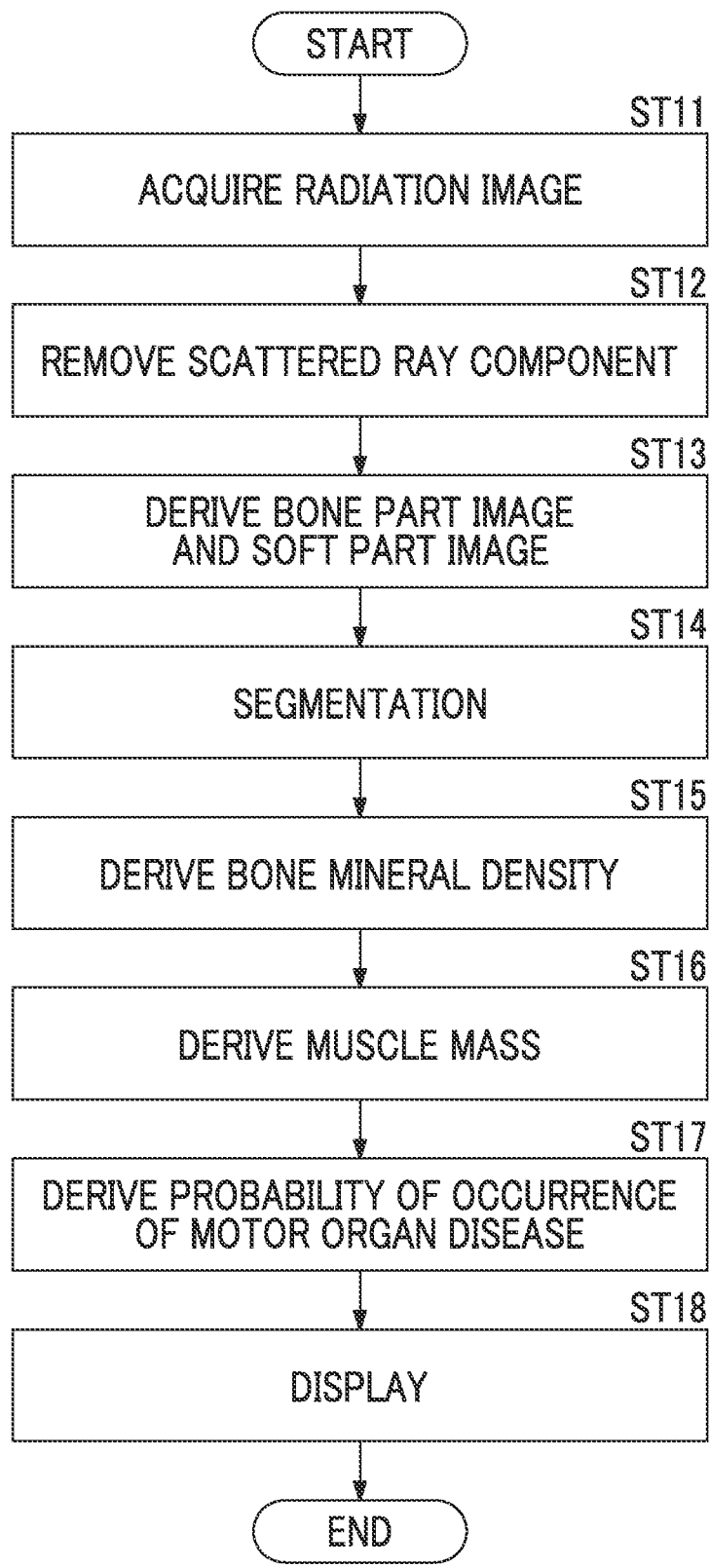
FIG. 20 is a flowchart of motor organ disease prediction processing performed in the present embodiment.

Then, motor organ disease prediction processing in the present embodiment will be described. FIG. 20 is a flowchart showing the motor organ disease prediction processing in the present embodiment. Note that the first and second radiation images G1 and G2 are acquired by imaging and stored in the storage 13. In a case in which an instruction for starting the processing is input from the input device 15, the image acquisition unit 21 acquires the first and second radiation images G1 and G2 from the storage 13 (radiation image acquisition; step ST11). Then, the scattered ray removal unit 31 of the information derivation unit 23 removes the scattered ray component from the first and second radiation images G1 and G2 (step ST12). In addition, the image derivation unit 32 derives the bone part image Gb in which the bone part of the subject H is extracted and the soft part image Gs in which the soft part is extracted from the first and second radiation images G1 and G2 (step ST13). Moreover, the segmentation unit 33 performs segmentation of the bone part image Gb into the region of the femur, the region of the pelvis, and the region of the vertebra, which are the target bones (step ST14).

Subsequently, the bone mineral density derivation unit 34 derives the bone mineral density for each pixel of the bone part image Gb (step ST15), and the muscle mass derivation unit 35 derives the muscle image Gm from the soft part image Gs and derives the muscle mass for each pixel of the muscle image Gm (step ST16).

Moreover, the probability derivation unit 24 derives the probability of occurrence of the motor organ disease relating to the target bone from the bone mineral density of the target bone, the muscle mass around the target bone, the shape information of the target bone, and the shape information of the bone adjacent to the target bone by using the learned neural network 24A (step ST17). Further, the display controller 26 displays the probability of occurrence of the motor organ disease derived by the probability derivation unit 24 on the display 14 (step ST18), and terminates the processing.

As described above, in the present embodiment, the probability of occurrence of the motor organ disease relating to the target bone is derived from the bone mineral density of the target bone, the muscle mass around the target bone, the shape information of the target bone, and the shape information of the bone adjacent to the target bone. Here, the fracture of the femur and the hip joint dislocation are likely to occur due to the reduction in the bone mineral density and the reduction in the muscle mass, but are also likely to occur in a case in which the hip joint is deformed from a normal state. In the present embodiment, the shape information of the femur, which is the target bone, and the shape information of the pelvis adjacent to the target bone are further used to derive the probability of occurrence of the motor organ disease, so that the occurrence of the motor organ disease can be predicted with higher accuracy.

In addition, by displaying the probability of occurrence of the motor organ disease, the probability of occurrence of the motor organ disease in the current situation can be easily recognized. In particular, it can be easily recognized how much bone mineral density and muscle mass need only be increased by further displaying the probability of occurrence of the motor organ disease in a case in which the bone mineral density and the muscle mass reach the target values.

In addition, it can be easily recognized about drugs which need only be given to the patient or the exercise recommended by the patient by further displaying the options for the medical intervention to make the bone mineral density and the muscle mass reach the target value.

Note that in the embodiment described above, the probability of occurrence of the fracture and the dislocation is derived as the probability of occurrence of the motor organ disease, but the probability of occurrence of any one of the fracture or the dislocation may be derived.

In addition, in the embodiment described above, the femur is used as the target bone, but the present disclosure is not limited to this. The target bone may be the vertebra, particularly the lumbar vertebra. The vertebra adjacent to the vertebra can be a vertebra adjacent above the vertebra, which is the target bone, a vertebra adjacent below the vertebra, and a vertebra adjacent above and below the vertebra.

The bone mineral density of the vertebra is reduced particularly due to the development of osteoporosis, and in a case in which osteoporosis worsens, the vertebra is compressed and deformed in a vertical direction of the human body, and further, a compression fracture occurs. Note that in a case in which the vertebra is the target bone, the dislocation is unlikely to occur. Therefore, in a case in which the target bone is the vertebra, the probability of occurrence of the fracture can be predicted with higher accuracy by using the shape information of the vertebra, which is the target bone, and the shape information of the vertebra adjacent to the target bone. In addition, in a case in which the target bone is the vertebra, it is preferable to display the exercise for training a back muscle as the medical intervention to be displayed.

In addition, in the present embodiment, in addition to the femur and the vertebra, any bone, such as the femur and a tibia around a knee joint can be used as the target bone.

In addition, in the embodiment described above, the bone mineral density and the muscle mass are derived by using the first radiation image G1 and the second radiation image G2 itself, but the present disclosure is not limited to this. For each pixel of the first radiation image G1 and the second radiation image G2, a movement average with the surrounding pixels is calculated, and the first radiation image G1 and the second radiation image G2 in which the movement average is used as the pixel value of each pixel may be used to derive the bone mineral density and the muscle mass. Here, since a cortical bone is important information in a case in which the bone mineral density is determined, the movement average with the surrounding pixels need only be calculated for each pixel such that a resolution at which the cortical bone can be visually recognized, for example, a resolution of equal to or smaller than 2 mm in the actual size of the subject is held. In this case, the pixels to be used as the movement average need only be appropriately determined from information on a mutual distance between the radiation source 3, the subject H, and the radiation detectors 5 and 6, information on a pixel size of the radiation detectors 5 and 6, and the like.

Figure 21:
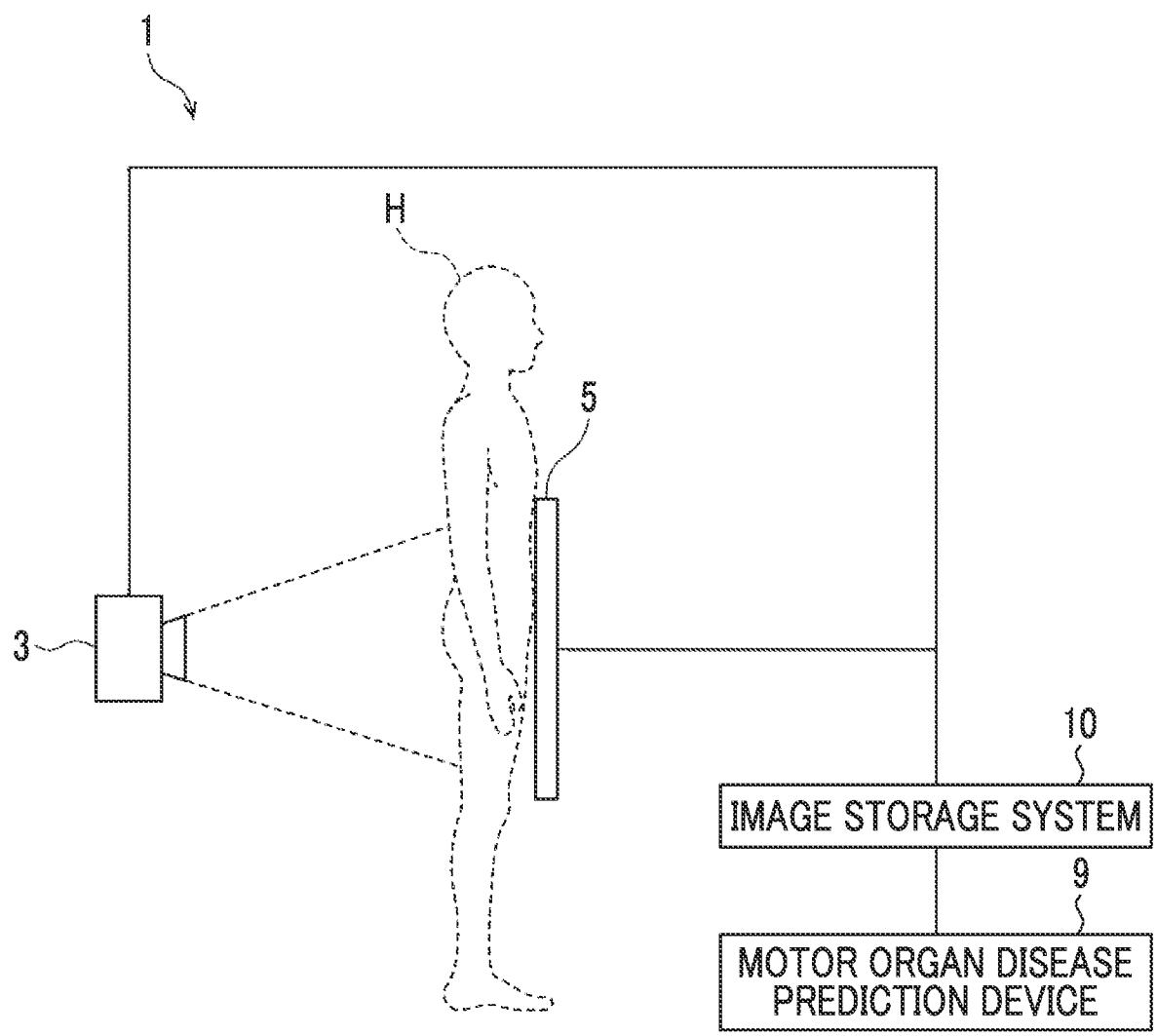
FIG. 21 is a schematic block diagram showing a configuration of a radiography system to which a motor organ disease prediction device and a learning device according to another embodiment of the present disclosure are applied.

In addition, in the embodiment described above, the first and second radiation images G1 and G2 are acquired by the one-shot method in a case in which the energy subtraction processing is performed, but the present disclosure is not limited to this. As shown in FIG. 21, the first and second radiation images G1 and G2 may be acquired by a so-called two-shot method in which imaging is performed twice by using only one radiation detector. In a case of the two-shot method, a position of the subject H included in the first radiation image G1 and the second radiation image G2 may shift due to a body movement of the subject H. Therefore, in the first radiation image G1 and the second radiation image G2, it is preferable to perform the processing according to the present embodiment after registration of the subject is performed. As registration processing, for example, a method disclosed in JP2011-255060A can be used. In the method disclosed in JP2011-255060A, for each of the first and second radiation images G1 and G2, a plurality of first band images and a plurality of second band images representing structures having different frequency bands are generated, a misregistration amount of the positions corresponding to each other in the first band image and the second band image of the corresponding frequency band is acquired, and the registration of the first radiation image G1 and the second radiation image G2 is performed based on the misregistration amount.

In addition, in the embodiment described above, the motor organ disease prediction processing is performed by using the radiation image acquired by the system that images the first and second radiation images G1 and G2 of the subject H by using the first and second radiation detectors 5 and 6, it is needless to say that the technology of the present disclosure can be applied to even in a case in which the first and second radiation images G1 and G2 are acquired by using an accumulative phosphor sheet instead of the radiation detector. In this case, the first and second radiation images G1 and G2 need only be acquired by stacking two accumulative phosphor sheets, emitting the radiation transmitted through the subject H, accumulating and recording radiation image information of the subject H in each of the accumulative phosphor sheets, and photoelectrically reading the radiation image information from each of the accumulative phosphor sheets. Note that the two-shot method may also be used in a case in which the first and second radiation images G1 and G2 are acquired by using the accumulative phosphor sheet.

In addition, in the embodiment described above, the target values of the bone mineral density and the muscle mass are plotted on the first and second graphs 51 and 52 on the display screen of the probability of occurrence of the motor organ disease, but the present disclosure is not limited to this. The probability of occurrence of the motor organ disease in a case in which the bone mineral density and the muscle mass are reduced without any treatment from now on, for example, in a case in which the bone mineral density and the muscle mass is reduced to ¼ may be plotted on the first and second graphs 51 and 52. As a result, it is possible to motivate the patient to be treated and to exercise.

In addition, the radiation in the embodiment described above is not particularly limited, and α-rays or γ-rays can be used in addition to X-rays.

In addition, in the embodiment described above, for example, various processors shown below can be used as the hardware structures of processing units that execute various pieces of processing, such as the image acquisition unit 21, the information acquisition unit 22, the information derivation unit 23, the probability derivation unit 24, the learning unit 25, and the display controller 26. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electric circuit that is a processor having a circuit configuration which is designed for exclusive use in order to execute specific processing, such as an application specific integrated circuit (ASIC).

One processing unit may be configured by one of these various processors, or may be a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer, such as a client and a server, there is an aspect in which one processor is configured by a combination of one or more CPUs and software and this processor functions as a plurality of processing units. Second, as represented by a system on chip (SoC) or the like, there is an aspect of using a processor that realizes the function of the entire system including the plurality of processing units by one integrated circuit (IC) chip. In this way, as the hardware structure, the various processing units are configured by using one or more of the various processors described above.

Moreover, as the hardware structures of these various processors, more specifically, it is possible to use an electrical circuit (circuitry) in which circuit elements, such as semiconductor elements, are combined.

What is claimed is:

1. A motor organ disease prediction device comprising:
   at least one processor,
   wherein the processor
      derives a bone mineral density of a target bone among bones included in a subject including a bone part and a soft part, a muscle mass around the target bone, shape information representing a shape of the target bone, and shape information representing a shape of a bone adjacent to the target bone from a first radiation image and a second radiation image acquired by imaging the subject by radiation having different energy distributions,
      derives a probability of occurrence of a motor organ disease relating to the target bone from the bone mineral density of the target bone, the muscle mass around the target bone, the shape information of the target bone, and the shape information of the bone adjacent to the target bone,
      displays the derived probability of occurrence of the motor organ disease on a display,
      displays a graph representing a relationship between at least one of the bone mineral density or the muscle mass and the probability of occurrence of the motor organ disease, and
      displays a plot representing the derived probability of occurrence of the motor organ disease and a plot representing a changed value of the probability of occurrence or at least one of the bone mineral density or the muscle mass on the graph.

2. The motor organ disease prediction device according to claim 1,
wherein the processor functions as a learned neural network which is machine-learned by using, as teacher data, the bone mineral density of the target bone among the bones included in a human body, the muscle mass around the target bone, the shape information representing the shape of the target bone, the shape information representing the shape of the bone adjacent to the target bone, and correct answer data representing the probability of occurrence of the motor organ disease relating to the target bone.

3. The motor organ disease prediction device according to claim 1,
wherein the changed value is a target value of at least one of the bone mineral density or the muscle mass, or a target value of the probability of occurrence of the motor organ disease.

4. The motor organ disease prediction device according to claim 3,
wherein the processor further displays an option of a medical intervention for making at least one of the bone mineral density or the muscle mass reach the target value, or an option of a medical intervention for making the motor organ disease reach the target value.

5. The motor organ disease prediction device according to claim 4,
wherein the medical intervention is an exercise method for training a muscle relating to the target bone.

6. The motor organ disease prediction device according to claim 1,
wherein the target bone is a femur.

7. The motor organ disease prediction device according to claim 1,
wherein the target bone is a vertebra.

8. The motor organ disease prediction device according to claim 1,
wherein the motor organ disease is at least one of a fracture or a dislocation.

9. A motor organ disease prediction method comprising:
deriving a bone mineral density of a target bone among bones included in a subject including a bone part and a soft part, a muscle mass around the target bone, shape information representing a shape of the target bone, and shape information representing a shape of a bone adjacent to the target bone from a first radiation image and a second radiation image acquired by imaging the subject by radiation having different energy distributions;
deriving a probability of occurrence of a motor organ disease relating to the target bone from the bone mineral density of the target bone, the muscle mass around the target bone, the shape information of the target bone, and the shape information of the bone adjacent to the target bone,
displaying the derived probability of occurrence of the motor organ disease on a display,
displaying a graph representing a relationship between at least one of the bone mineral density or the muscle mass and the probability of occurrence of the motor organ disease, and
displaying a plot representing the derived probability of occurrence of the motor organ disease and a plot representing a changed value of the probability of occurrence or at least one of the bone mineral density or the muscle mass on the graph.

10. A non-transitory computer-readable storage medium that stores a motor organ disease prediction program causing a computer to execute:
a procedure of deriving a bone mineral density of a target bone among bones included in a subject including a bone part and a soft part, a muscle mass around the target bone, shape information representing a shape of the target bone, and shape information representing a shape of a bone adjacent to the target bone from a first radiation image and a second radiation image acquired by imaging the subject by radiation having different energy distributions;
a procedure of deriving a probability of occurrence of a motor organ disease relating to the target bone from the bone mineral density of the target bone, the muscle mass around the target bone, the shape information of the target bone, and the shape information of the bone adjacent to the target bone;
a procedure of displaying the derived probability of occurrence of the motor organ disease on a display,
a procedure of displaying a graph representing a relationship between at least one of the bone mineral density or the muscle mass and the probability of occurrence of the motor organ disease, and
a procedure of displaying a plot representing the derived probability of occurrence of the motor organ disease and a plot representing a changed value of the probability of occurrence or at least one of the bone mineral density or the muscle mass on the graph.

* * * * *